US005443969A

United States Patent [19]

Wilson et al.

[11] Patent Number: 5,443,969

[45] Date of Patent: Aug. 22, 1995

[54] RNA PACKAGING SYSTEM

[75] Inventors: Thomas M. A. Wilson, Dundee, Scotland; Duk-Ju Hwang-Lee, Piscataway, N.J.

[73] Assignee: Rutgers University, New Brunswick, N.J.

[21] Appl. No.: 971,101

[22] Filed: Oct. 29, 1992

[51] Int. Cl.[6] ........................ C12N 15/10; C12N 1/21; C12N 15/40; C12N 7/01

[52] U.S. Cl. .............................. 435/91.32; 435/172.3; 435/235.1; 435/252.3; 435/252.33; 435/810; 536/23.72; 422/61

[58] Field of Search .................... 435/172.3, 91, 235.1, 435/252.3, 252.33, 317.1, 810, 91.32, 975; 206/223; 935/16; 422/61; 536/23.72

[56] References Cited

FOREIGN PATENT DOCUMENTS

WO8706261 10/1987 WIPO .......................... C12N 15/00

OTHER PUBLICATIONS

Schein, C. H. 1989, Bio/Technology vol. 7 pp. 1141–1149.

Sleat, D. E. et al. 1988, Nucleic Acids Res. vol. 16 pp. 3127–3140.

Jagadish et al., 1991, Expression of potyvirus coat protein in *Escherichia coli* and yeast and its assembly into virus-like particles, J. Gen. Virol. 72:1543–50.

Guo et al., 1991, sRNA of Phage o29 of *Bacillus subtilis* mediates DNA packaging of o29 proheads assembled in *Escherichia coli,* Virol. 185:395–400.

Olkkonen et al., 1990, In vitro assembly of infectious nucleocapsids of bacteriophage o6: formation of a recombinant double-stranded RNA virus, Proc. Natl. Acad. Sci. USA 87:9173–77.

Gal-On et al., 1990, Nucleotide sequence of the zucchini yellow mosaic virus capsid-encoding gene and its expression in *Escherichia coli,* Gene 87:273–77.

Shire et al., 1990, Preparation and properties of recombinant DNA derived tobacco mosaic virus coat protein, Biochem. 29:5119–26.

Duda et al., 1990, Expression of plasmid-encoded structural proteins permits engineering of bacteriophage T4 assembly, Virol. 179:728–37.

Studier et al., 1990, Use of T7 RNA polymerase to direct expression of cloned genes, Meth. Enzymol. 185:60–89.

Wilson et al., 1990, Effects of the 5'-leader sequence of tobacco mosaic virus RNA, or derivatives thereof, on foreign mRNA and native viral gene expression, Post--Transcriptional Control of Gene Expression in NATO ASI Series, vol. H 49, J. E. G. McCarthy and M. F. Tuite (eds.), Springer-Verlag Berlin Heidelberg.

(List continued on next page.)

*Primary Examiner*—Mary E. Mosher
*Attorney, Agent, or Firm*—Pennie & Edmonds

[57] ABSTRACT

The present invention relates to an in vivo system for expression and packaging of recombinant RNA into pseudovirus particles. The invention is based on the discovery that plant viral coat proteins (CPs) may be efficiently expressed in *E. coli,* and that these recombinant coat proteins will function to assemble in vivo and package recombinant chimeric RNA, containing an operatively linked origin-of-assembly (OAS) sequence, to form mature viral particles containing a foreign RNA. The present invention thus provides for packaging of RNA into a ribonuclease-resistant form that is easily purified and stored, and which overcomes the prior art problems associated with degradation of RNA by ribonucleases. Significantly, the method of the invention is RNA sequence- and length-independent. The components of the invention include a source in the bacterial host of viral coat proteins, and a source in the bacterial host to direct the transcription of a DNA molecule comprising an OAS-encoding DNA and a foreign DNA, which DNA molecule can be transcribed in the host cell to produce an RNA molecule comprising an OAS operatively linked to an RNA of interest. The CPs and OAS are from a plant virus having a rod-shaped helical particle and a single-stranded RNA genome, most preferably tobacco mosaic virus.

68 Claims, 12 Drawing Sheets

OTHER PUBLICATIONS

Turner et al., 1988, The tobacco mosaic virus assembly original RNA. Functional characteristics defined by directed mutagenesis, J. Mol. Biol. 203:531–47.
Jupin et al., 1989, Direct recovery of in vitro transcripts in a protected form suitable for prolonged storage and shipment at ambient temperatures, Nucl. Acids Res. 17:815.
Rosenberg and Studier, 1987, T7 RNA polymerase can direct expression of influenza virus capbinding protein (PB2) in *Escherichia coli*, Gene 59:191–200.
Gallie et al., 1987, In vivo uncoating and efficient expression of foreign mRNAs packaged in TMV–like particles, Science 236:1122–24.
Turner and Butler, 1986, Essential features of the assembly origin of tobacco mosaic virus RNA as studied by directed mutagenesis, Nucl. Acids Res. 14:9229–42.
Sleat et al., 1986, Packaging of recombinant RNA molecules into pseudovirus particles directed by the origin–of–assembly sequence from tobacco mosaic virus RNA, Virol. 155:299–308.
Haynes et al., 1986, Development of a genetically–engineered, candidate polio vaccine employing the self–assembling properties of the tobacco mosaic virus coat protein, Bio/Tech. 4:637–41.
Rochon et al., 1986, Encapsidation of 18 S rRNA by tobacco mosaic virus coat protein, Virology 150:140–48.
Rochon and Siegel, 1984, Chloroplast DNA transcripts are encapsidated by tobacco mosaic virus coat protein, Proc. Natl. Acad. Sci. USA 81:1719–23.
Zimmern and Hunter, 1983, Point mutation in the 30–K open reading frame of TMV implicated in temperature–sensitive assembly and local lesion spreading of mutant Ni 2519, The EMBO Journal 2:1893–1900.
Zimmern, 1983, An extended secondary structure model for the TMV assembly origin, and its correlation with protection studies and an assembly defective mutant, The EMBO Journal, 2:1901–07.
Goelet et al., 1982, Nucleotide sequence of tobacco mosaic virus RNA, Proc. Natl. Acad. Sci. USA 79:5818–22.
Meshi et al., Nucleotide sequence of a cloned cDNA copy of TMV (cowpea strain) RNA, including the assembly origin, the coat protein cistron, and the 3′ non–coding region, Mol. Gen. Genet. 184:20–25.
Koenig and Lesemann, Aug. 1978, Potexvirus Group, in CMI/AAB Description of Plant Viruses. No. 200, Commonwealth Agricultural Bureaux and the Association of Applied Biologists.
Gibbs, Sep. 1977, Tobamovirus Group, in CMI/AAB Description of Plant Viruses. No. 184, Commonwealth Agricultural Bureaux and the Association of Applied Biologists.
Guilley et al., 1975, Observations concerning the sequence of two additional specifically encapsidated RNA fragments originating from the tobacco–mosaic–virus coat–protein cistron, Eur. J. Biochem. 54:145–53.
Guilley et al., 1975, Sequence of a specifically encapsidated RNA fragment originating from the tobacco–mosaic–virus coat–protein cistron, Eur. J. Biochem. 54:135–44.
Zimmern, 1975, The 5′ end group of tobacco mosaic virus RNA is $m^7G^{5'}ppp^{5'}Gp$, Nuc. Acids Res. 2:1189–1201.
Harrison, Jul., 1973, Pea Early–Browning Virus, in CMA/AAB Description of Plant Viruses. No. 120, Commonwealth Agricultural Bureaux and the Association of Applied Biologists.
Fritsch et al., 1973, Specificity of TMV RNA Encapsidation: in vitro coating of heterologous RNA by TMV protein, Virol. 56:33–45.
Durham, 1972, The cause of irreversible polymerisation of tobacco mosaic virus protein, FEBS Lett. 25:147–52.
Durham, 1972, Structures and roles of the polymorphic forms of tobacco mosaic virus protein, J. Mol. Biol. 67:289–305.
Siegel, 1971, Pseudovirions or tobacco mosaic virus, Virology 46:50–59.
Harrison, Jun., 1970, Tobacco Rattle virus, in CMA-/AAB Description of Plant Viruses. No. 12, Commonwealth Agricultural Bureaux and the Association of Applied Biologists.
Sugiyama, 1966, Tobacco mosaic viruslike rods formed by "mixed reconstitution" between MS2 ribonucleic acid and tobacco mosaic virus protein, Virology 28:488–492.
Turner et al., 1989, "Assembly of hybrid RNAs with tobacco mosaic virus coat protein. Evidence for incorporation of disks in 5′ elongation along the major RNA tail," J. Mol. Biol. 209:407–422.
(List continued on next page.)

OTHER PUBLICATIONS

Gallie et al., 1987, "The effect off multiple dispersed copies of the origin–of–assembly sequence from TMV RNA on the morphology of pseudovirus particles assembled in vitro," Virology 158:473–476.

Goulden et al., 1992, "Structure of tobraviral particles: a model suggested from sequence conservation in tobraviral and tobamoviral coat proteins," J. Mol. Biol. 227:1–8.

Dolja et al., 1991, "Phylogeny of capsid proteins of rod shaped and filamentous RNA plant viruses: two families with distinct patterns of sequence and probably structure conservation," Virology 184:79–86.

Sacher et al., 1988, "Hybrid brome mosaic virus RNAs express and are packaged in tobacco mosaic virus coat protein in vivo," virology 167:15–24.

FIG. 6
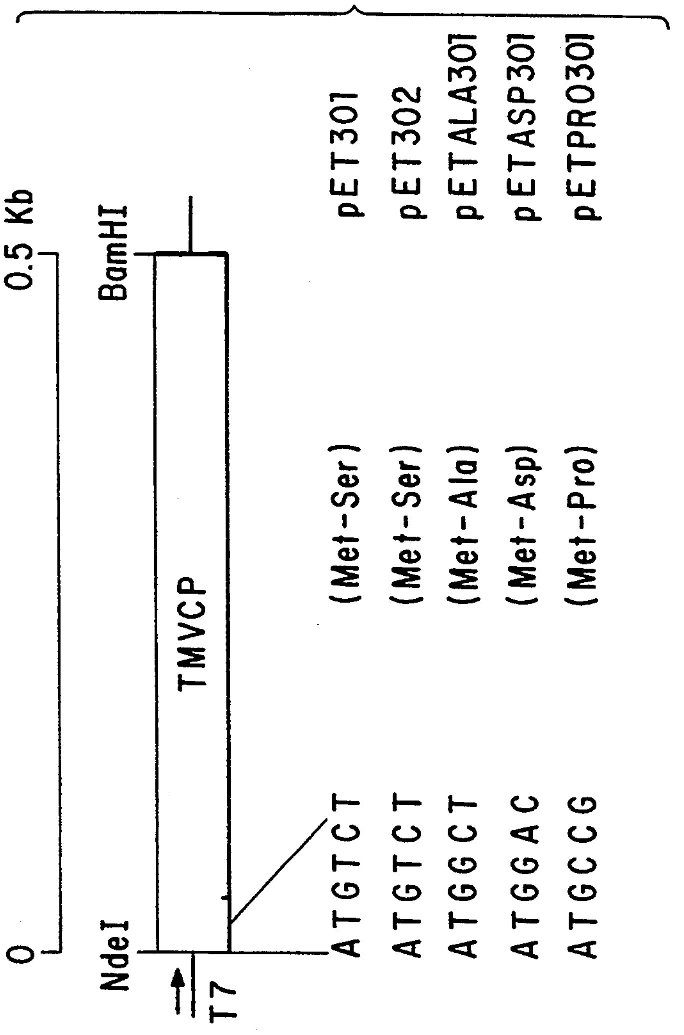
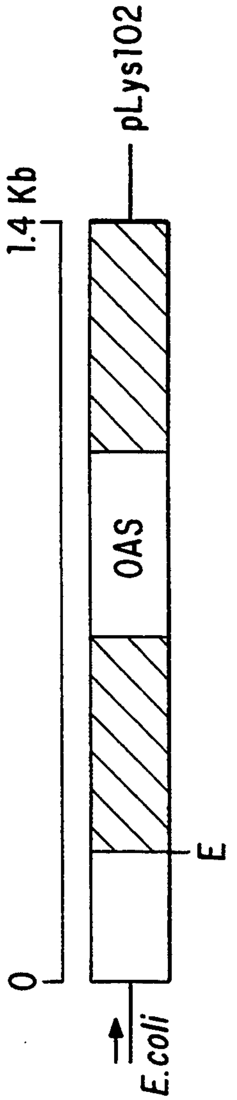
FIG. 7

5118

GGUCGUCACG GGCGAGUGGA ACUUGCCUGA CAAUUGCAGA GGAGGUGUGA GCGUGUGUCU 60

GGUGGACAAA AGGAUGGAAA GAGCCGACGA GGCCACUCUC GGAUCUUACU ACACAGCAGC 120

UGCAAAGAAA AGAUUUCAGU UCAAGGUCGU UCCCAAUUAU GCUAUAACCA CCCAGGACGC 180

GAUGAAAAAC GUCUGGCAAG UUUUAGUUAA UAUUAGAAAU GUGAAGAUGU CAGCGGGUUU 240

CUGUCCGCUU UCUCUGGAGU UUGUGUCGGU GUGUAUUGUU UAUAGAAAUA AUAUAAAAUU 300

AGGUUUGAGA GAGAAGAUUA CAAACGUGAG AGACGGAGGG CCCAUGGAAC UUACAGAAGA 360

AGUCGUUGAU GAGUUCAUGG AAGAUGUCCC UAUGUCGAUC AGGCUUGCAA AGUUUCGAUC 420

UCGAACCGGA AAA 433

UGAGAGACGG AGGGCCCAUG GAACUUACAG AAGAAGUCGU UGAUGAGUUC AUGGAAGAUG 60
UCCCUAUGUC GAUCA 75

FIG.11

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 24 nucleotides
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:1:

GCCATGGCTT ACAGTATCAC TACT 24

-continued ( 2 ) INFORMATION FOR SEQ ID NO:2:

( i ) SEQUENCE CHARACTERISTICS:
( A ) LENGTH: 24 nucleotides
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:2:

GGTCGACCTC AAGTTGCAGG ACCA 24

( 2 ) INFORMATION FOR SEQ ID NO:3:

( i ) SEQUENCE CHARACTERISTICS:
( A ) LENGTH: 24 nucleotides
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:3:

GCCATGGACT ACAGTATCAC TACT 24

( 2 ) INFORMATION FOR SEQ ID NO:4:

( i ) SEQUENCE CHARACTERISTICS:
( A ) LENGTH: 24 nucleotides
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:4:

GGCATGCCGT ACAGTATCAC TACT 24

( 2 ) INFORMATION FOR SEQ ID NO:5:

( i ) SEQUENCE CHARACTERISTICS:
( A ) LENGTH: 433 nucleotides
( B ) TYPE: nucleic acid
( C ) STRANDEDNESS: single
( D ) TOPOLOGY: unknown ( i i ) MOLECULE TYPE: RNA ( x i ) SEQUENCE DESCRIPTION: SEQ ID NO:5:

GGUCGUCACG GGCGAGUGGA ACUUGCCUGA CAAUUGCAGA GGAGGUGUGA GCGUGUGUCU 60

GGUGGACAAA AGGAUGGAAA GAGCCGACGA GGCCACUCUC GGAUCUUACU ACACAGCAGC 120

UGCAAAGAAA AGAUUUCAGU UCAAGGUCGU UCCCAAUUAU GCUAUAACCA CCCAGGACGC 180

GAUGAAAAAC GUCUGGCAAG UUUUAGUUAA UAUUAGAAAU GUGAAGAUGU CAGCGGGUUU 240

CUGUCCGCUU UCUCUGGAGU UUGUGUCGGU GUGUAUUGUU UAUAGAAAUA AUAUAAAAUU 300

AGGUUUGAGA GAGAAGAUUA CAAACGUGAG AGACGGAGGG CCCAUGGAAC UUACAGAAGA 360

AGUCGUUGAU GAGUUCAUGG AAGAUGUCCC UAUGUCGAUC AGGCUUGCAA AGUUUCGAUC 420

UCGAACCGGA AAA 433

( 2 ) INFORMATION FOR SEQ ID NO:6:

( i ) SEQUENCE CHARACTERISTICS:
( A ) LENGTH: 75 nucleotides
( B ) TYPE: nucleic acid
( C ) STRANDEDNESS: single -continued ( D ) TOPOLOGY: unknown ( i i ) MOLECULE TYPE: RNA ( x i ) SEQUENCE DESCRIPTION: SEQ ID NO:6:

UGAGAGACGG AGGGCCCAUG GAACUUACAG AAGAAGUCGU UGAUGAGUUC AUGGAAGAUG 60

UCCCUAUGUC GAUCA 75

( 2 ) INFORMATION FOR SEQ ID NO:7:

( i ) SEQUENCE CHARACTERISTICS:
( A ) LENGTH: 15 nucleotides
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:7:

CCGGTTCGAG ATCGA 15

( 2 ) INFORMATION FOR SEQ ID NO:8:

( i ) SEQUENCE CHARACTERISTICS:
( A ) LENGTH: 14 nucleotides
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:8:

GTTGGTCGTC ACGG 14

RNA PACKAGING SYSTEM

INTRODUCTION

The present invention relates to an in vivo system for expression and packaging of recombinant single-stranded RNA of unlimited length or sequence into pseudovirus particles comprised of plant viral coat proteins. The invention provides a means for efficient production and long-term handling and storage of otherwise labile RNA in ribonuclease-resistant virus-like particles.

BACKGROUND OF THE INVENTION

A number of infectious plant viruses, including members of the Tobamo-, Potex-, Poty- and Tobra-groups of viruses, share properties in common with one another. These properties include a single-stranded RNA genome encapsidated by viral coat protein oligomers that assemble to form either elongated rigid rods or flexuous threads.

Perhaps the best studied of the plant viruses is the tobamovirus Tobacco Mosaic Virus (TMV) which has a genome size of 6.4 Kb. The positive stranded genomic RNA codes for a number of viral proteins including those required for replication of the viral genome and those coding for structural proteins such as the coat protein which assembles into 20S protohelical or disk-like structures that become arranged into elongated helical structures with the viral genomic RNA molecule (Goelet et al., 1982, Proc. Natl. Acad. Sci. 79:5818–22).

Contiguous with the TMV genomic RNA is a sequence element referred to as the origin-of-assembly sequence (OAS) that is necessary and sufficient to direct efficient encapsidation of contiguous viral RNA sequences into virus particles. The TMV OAS is located approximately 1 Kb from the 3′ end of the viral genome in the common strain (and in the coat protein gene itself in the cowpea strain (Cc; Sunn-hemp mosaic virus)) and consists of a 440 nucleotide sequence that is predicted to form three hairpin stem-loop structures (Turner and Butler, 1986, Nucl. Acids Res. 14:9229–42). The viral coat protein disks initially bind to loop 1 (the 3′ most) during viral be assembly and in vitro packaging assays using mutant assembly origin transcripts have defined the 75 nucleotides comprising loop 1 as necessary and sufficient for encapsidation of foreign or viral RNA sequences (Turner et al., 1988, J. Mol. Biol. 203:531–47).

In vitro reconstitution studies have provided details on the assembly process for TMV. Preparations of purified coat protein, derived from virions from infected plant cells, are able to assemble into helical structures and virus-like rods, even in the absence of RNA at pH 5, suggesting that the coat protein contains the essential information required for self-assembly. Incubation of purified TMV coat protein preparations with TMV RNA at pH 7, in vitro, results in assembly of TMV-like viral particles containing encapsidated RNA (Fraenkel-Conrat and Williams, 1955, Proc. Natl. Acad. Sci. 41:690–98). Furthermore, it has been shown that foreign chimeric RNA molecules containing OAS sequences, transcribed in 30 vitro using SP6 or T7 (Jupin, I. et al., 1989, Nucl. Acids Res. 17:815) transcription plasmids can also be assembled in vitro into pseudovirus particles (Sleat et al., 1986, Virology 155:299–308).

Until recently, sources of viral coat proteins for in vitro reconstitution studies have relied on virus preparations made from infected plant tissue. However, such sources are disadvantageous since laborious procedures comprising infection with virus, purification of the virus from plant tissue, and then purification of coat protein from the virus must be used. The cloning and sequencing of a number of plant viral genomes has led to the identification of viral coat protein encoding sequences. Insertion of these genes into bacterial expression vectors has allowed the expression of, for instance, TMV coat protein in *E. coli* (Shire et al., 1990, Biochemistry 29:5119–26). However, it was reported (id.) that recombinant TMV coat protein produced in *E. coli* reconstitutes in vitro with TMV RNA at a greatly reduced rate relative to the reconstitution with native coat protein; the authors suggested that this inefficiency in reconstitution arises from the lack of an acetyl group on the amino terminus of the recombinant protein, which is present on the native coat protein. Zucchini yellow mosaic virus and Johnsongrass mosaic virus (both potyviruses, which are not members of the tobamovirus, tobravirus, or potexvirus groups) coat proteins have also been produced in *E. coli* (Gal-On et al., 1990, Gene 87:273–277; Jagadish et al. 1991, J. Gen. Virology 72:1543–1550).

Present work in molecular biology and recombinant nucleic acid technology is encumbered by problems associated with degradation of RNA by ribonucleases. Researchers in the past have relied on inhibitors such as human placental RNase inhibitor (RNAsin), or the use of alkylating reagents such as diethylpyrocarbonate (DEPC) which is a suspected carcinogen to inhibit the activity of ribonucleases; such inhibitors may produce (DEPC) undesirable modified components of RNA.

SUMMARY OF THE INVENTION

The present invention relates to an in vivo system for expression and packaging of recombinant single-stranded RNA into pseudovirus particles. The invention is based on the discovery that viral coat proteins (CPs) may be efficiently expressed in *E. coli*, and that these recombinant coat proteins will function to assemble in vivo and package recombinant chimeric RNA, containing a contiguous origin-of-assembly sequence (OAS), to form mature virus-like particles containing a foreign RNA. The present invention thus provides for packaging of RNA into a ribonuclease-resistant form that is easily purified and stored, and which overcomes the prior art problems associated with degradation of RNA by ribonucleases. The invention provides for convenient, efficient production and long-term storage of any RNA of interest, without substantial degradation. Significantly, the method of the invention is RNA sequence- and length-independent. The in vivo system provided herein for production and packaging of recombinant RNA will have broad applications that will include any of the techniques currently used by molecular biologists involving manipulation of RNA. These include for example in vitro translation reactions to produce proteins of interest, synthesis of sense and antisense RNA molecules for introduction into cells to study protein function, and synthesis of radiolabelled RNA probes for use in Northern or Southern Blot analyses.

The components of the invention include a source in the bacterial host of viral coat proteins, and a source in the bacterial host to direct the transcription of a DNA molecule comprising an OAS encoding DNA linked to a foreign DNA (hereinafter "*DNA"), which DNA molecule can be transcribed in the host cell to produce an RNA molecule comprising an OAS linked to an RNA of interest (hereinafter "OAS-linked *RNA"); both sources being compatible and capable of protein (CP) expression and transcription (of OAS-linked *DNA), respectively, together in the same bacterial host. The CPs and OAS provided by the invention can be that of any plant virus having a rod-shaped helical particle and a single-stranded RNA genome, including but not limited to a tobamovirus, potexvirus, tobravirus, hordeivirus, potyvirus, and furovirus. In a preferred aspect, the sources of the CP and OAS-linked *DNA are plasmid vectors. In a specific embodiment, a single plasmid vector is the source of both CP and OAS-linked *RNA. In another embodiment, the different sources are different plasmid vectors. Vectors, recombinant cells, and kits for carrying out the method of the invention are also provided.

DESCRIPTION OF THE FIGURES

FIG. 6. Schematic diagram of a portion of the pET3a vector derivatives encoding TMV CP. The thin line represents the pET3a vector sequence. The site directed mutagenesis of the 5′ end of the gene encoding TMV CP was done by PCR reactions. The mutated gene encoding TMV CP was cloned into the final expression vector, pET3a, using the NdeI and BamHI sites.

FIG. 7. Vector providing OAS-linked ,DNA. A schematic diagram of a portion of the pLys102 vector providing the transcript to be packaged in *E. coli*, comprising the OAS-linked CAT DNA, is shown. OAS is the origin of assembly sequence of TMV. The hatched area shows a repeated sequence of the CAT gene generated by cloning-in the OAS cassette.

FIG. 10. TMV origin of assembly. The nucleotide sequence from nucleotides 5118–5550 (SEQ ID NO:5) of the TMV genome (from Goelet et al., 1982, Proc. Natl. Acad. Sci. USA 79:5818–22), containing the TMV OAS extending from bases 5290 to 5527 of the viral sequence (nucleotides 173–410 in SEQ ID NO:5) (Zimmern, D., 1983, EMBO J. 2:1901–07), is shown.

FIG. 11. Loop 1 of TMV OAS. The nucleotide sequence (SEQ ID NO:6) is shown of loop 1 of the TMV OAS, which is known to be sufficient to direct the encapsidation of a contiguous RNA fragment by TMV coat protein disks (from Turner, D. R., et al., 1988, J. Mol. Biol. 203:531–47; FIG. 1).

DETAILED DESCRIPTION OF THE INVENTION

Figure 1:
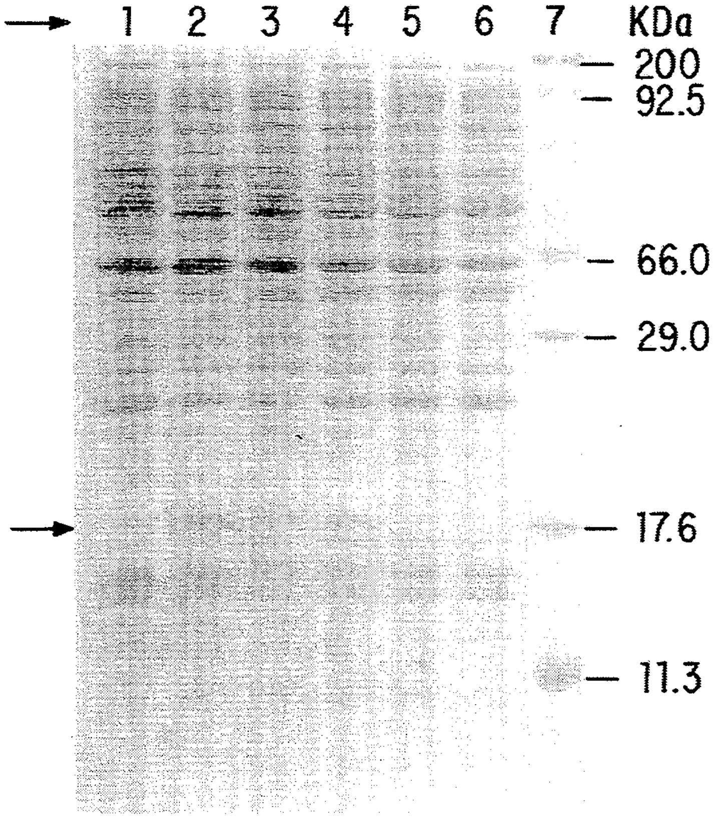
FIG. 1. Coomassie stained (15%) polyacrylamide gel of TMV coat proteins expressed in *E. coli*. Lanes: 1, pETPro301 (+) IPTG; 2, pET302 (+) IPTG; 3, pETAla301 (+) IPTG; 4, pET301 (+)IPTG; 5, pET3a (+) IPTG; 6, pET3a (−) IPTG; 7, protein size markers.

The present invention relates to an in vivo system for production and packaging of recombinant single-stranded RNA into pseudovirus (virus-like) particles. The in vivo packaging system is useful as a means of producing significant amounts of RNA of interest in a form that is both easily purified and protected from the degradative effects of ribonucleases.

The invention is based on the ability to express, in vivo, viral coat proteins (CPs) and package chimeric recombinant RNA containing OAS-linked sequences (hereinafter "OAS-linked *RNA") such that the CPs function to assemble and package the OAS-linked *RNA into pseudovirus particles. As will be apparent, "OAS-linked *DNA" refers herein to a DNA molecule comprising a sequence which can be transcribed to an OAS RNA sequence linked to an RNA of interest, while "OAS-linked *RNA" refers to the RNA sequence thus produced by such transcription. The components of the invention include sources for production within a bacterial host of both the viral CPs and the OAS-linked *RNA. In one aspect, the recombinant CP gene may be integrated into a bacterial host chromosome (e.g., by homologous recombination; see, e.g., Koller and Smithies, 1989, Proc. Natl. Acad. Sci. 86:8932–35; Zijlstra et al., 1989, Nature 342:435–38) for expression therefrom, and the OAS-linked ,DNA construct may be integrated into a bacterial host chromosome (e.g., by homologous recombination) for transcription therefrom. In an alternative, preferred embodiment, the CP is expressed from a vector, preferably a plasmid expression vector, and the OAS-linked *DNA is transcribed from a vector, preferably a plasmid expression vector, which can be the same or a different vector from the expression vector encoding the CP. Sources of the CP and OAS-linked *RNA according to the invention are detailed below.

PRODUCTION OF VIRAL COAT PROTEIN IN A BACTERIAL HOST

A first component of the invention is a source providing for recombinant production in a bacterial host of a plant viral CP. In a preferred aspect, the CP nucleic acid encodes a CP of a virus that is the same virus strain from which the OAS is derived.

The plant viral CP is the CP of a plant virus having a rod-shaped helical particle and a single-stranded RNA genome, including but not limited to a tobamovirus, potexvirus, tobravirus, hordeivirus, potyvirus, and furovirus, with the tobamovirus TMV most preferred. These virus groups have rod-shaped helical particles of lengths determined only by the size of the RNA therein; i.e., there are no packaging size constraints. Both natural viral strains and nitrous acid- and other induced mutant strains are contemplated as included in the foregoing virus groups. Members of the tobamovirus group include but are not limited to TMV, cucumber green mottle mosaic virus, tomato mosaic virus, Frangipani mosaic virus, Odontoglossum ringspot virus, Holmes' Ribgrass mosaic virus, sammons' Opuntia virus, Sunnhemp mosaic virus (cowpea Cc), U2-tobacco mosaic virus, etc. (see, e.g., CMI/AAB Descriptions of Plant Viruses, September 1977, No. 184). Tobraviruses include but are not limited to pea early-browning virus, tobacco rattle virus, and pepper ringspot virus. Potexviruses include but are not limited to potato virus X and papaya mosaic virus. Hordeiviruses include but are not limited to barley stripe mosaic virus. Potyviruses include but are not limited to potato virus Y. Furoviruses include but are not limited to soil-borne wheat mosaic virus, beet necrotic yellow vein virus, and potato moptop virus.

The nucleic acid encoding the CP is obtained by any means available in the art. Various CP nucleic acid sequences have been disclosed and can be used. For example, the TMV CP has been cloned and sequenced (see Goelet et al., 1982, Proc. Natl. Acad. Sci. 79:5818–22). Additionally, the sequence of a TMV CP gene with codons optimized for translation in a prokaryotic system has been disclosed (Haynes et al., 1986, Biotechnology 4:637–41). If a nucleic acid clone of the desired CP is not already available, the clone can be obtained by use of standard recombinant DNA methodology. For example, the DNA may be obtained by standard procedures known in the art from cloned DNA (e.g., a DNA "library"), by chemical synthesis, or by isolation of the viral RNA or fragments thereof, purified, preferably, from viral particles (see, for example Sambrook et al., 1989, Molecular Cloning, A Laboratory Manual, 2nd Ed., Cold Spring Harbor Laboratory, Cold Spring Harbor, N.Y.; Glover, D. M. (ed.), 1985, DNA Cloning: A Practical Approach, MRL Press, Ltd., Oxford, U.K. Vol. I, II.)

Identification of the specific DNA fragment containing the desired gene may be accomplished in a number of ways. For example, if an amount of a portion of a CP DNA or its specific RNA, or a fragment thereof, is available and can be purified and labeled, the generated DNA or RNA may be screened by nucleic acid hybridization to the labeled probe (Benton, W. and Davis, R., 1977, Science 196:180; Grunstein, M. and Hogness, D., 1975, Proc. Natl. Acad. Sci. U.S.A. 72:3961). Those DNA fragments with substantial homology to the probe will hybridize. It is also possible to identify the appropriate DNA by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, a cDNA clone can be selected which produces a CP that, e.g., has similar or identical electrophoretic migration, isolectric focusing behavior, proteolytic digestion maps, self-assembly activity or antigenic properties as known for the purified CP.

An appropriate CP RNA can also be identified by in vitro translation. Immunoprecipitation analysis or functional assays (e.g., self-assembly ability in vitro) of the in vitro translation products of the isolated RNA identifies the RNA as one containing the desired sequences.

Alternatives to isolating a CP gene include, but are not limited to, chemically synthesizing the gene sequence itself from a known sequence or making cDNA to the RNA which encodes the CP. Other methods are possible and within the scope of the invention.

If desired, the identified and isolated gene can then optimally be inserted into an appropriate cloning vector prior to transfer to a bacterial expression vector of the invention.

Nucleic acids which encode derivatives (including fragments) and analogs of native CPs can also be used in the present invention, as long as such derivatives and analogs retain the ability to assemble into a viral particle and package therein an OAS-containing RNA. In particular, CP derivatives can be made by altering CP sequences by substitutions, additions, or deletions that provide for functionally active molecules. Furthermore, due to the inherent degeneracy of nucleotide coding sequences, other DNA sequences which encode substantially the same or a functionally equivalent viral CP amino acid sequence may be used in the practice of the methods of the invention. For example, it may be useful to change DNA sequences to optimize for *E. coli* or other bacteria codon usage, or changes may be made in amino acid sequences to enhance viral particle assembly in the bacterial host system. Such alterations of the coat nucleotide sequence include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, Solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

In a specific embodiment, nucleic acids can be made which encode a CP fusion protein derivative which comprises a surface ligand fused via a peptide bond to the CP, such that the presence of the surface ligand does not interfere with OAS-dependent RNA assembly. "Surface ligand" as used herein refers to a peptide or protein which binds to a receptor on the surface of a cell. Thus, such surface ligand-CP fusion proteins can target the pseudovirus particle in vivo to a particular cell type expressing the receptor for the surface ligand; subsequent receptor-mediated endocytosis can effect intracellular delivery of the particle and its contained RNA into the cell. Surface ligands which can be used include but are not limited to peptides containing the Arg-Gly-Asp amino acid motif (the ligand for the polio receptor), asialoglycoprotein, etc.

Derivatives or analogs of CPs also include but are not limited to those peptides which are substantially homologous to CP or fragments thereof, or whose encoding nucleic acid is capable of hybridizing to a CP nucleic acid sequence, which are functionally active in assembly and packaging.

The nucleic acids encoding derivatives and analogs of the CP can be produced by various methods known in the art. For example, the cloned CP gene sequence can be modified by any of numerous strategies known in the art (Sambrook et al., 1989, Molecular Cloning, A Laboratory Manual, 2nd ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of a CP, care should be taken to ensure that the modified gene remains within the same translational reading frame as the CP, uninterrupted by translational stop signals, in the gene region where the CP functional activity is encoded.

Additionally, the CP-encoding nucleic acid sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used, including but not limited to, in vitro site-directed mutagenesis (Hutchinson, C., et al., 1978, J. Biol. Chem 253:6551).

The desired CP-encoding nucleic acid is then preferably inserted into an appropriate bacterial expression vector, i.e., a vector which contains the necessary elements for the transcription and translation of the inserted protein-coding sequence in a bacterial host, to create a vector that functions to direct the synthesis of the CP that will subsequently assemble and encapsidate the OAS-linked *RNA within the bacterium. A variety of vector systems may be utilized to express the CP-coding sequence, but the vector must be functional in the bacterial host and compatible with any other vector present (e.g., a vector containing the OAS-linked *DNA). Such vectors include but are not limited to bacteriophages, plasmids, or cosmids. In a preferred aspect, a plasmid expression vector is used. The expression elements of vectors vary in their strengths and specificities. Any one of a number of suitable transcription and translation elements may be used, as long as they are functional in the bacterial host.

Standard recombinant DNA methods may be used to construct expression vectors containing a chimeric gene consisting of appropriate transcriptional/translational control signals and the CP coding sequences (see, e.g., Sambrook et al., 1989, supra). These methods may include in vitro recombinant DNA and synthetic techniques and in vivo recombinants (genetic recombination). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and CP gene may be modified by homopolymeric tailing. Expression of the nucleic acid sequence encoding the CP may be regulated by a second nucleic acid sequence. For example, expression of a CP may be controlled by any bacterial promoter/enhancer element known in the art. Promoters which may be used to control CP gene expression can be constitutive or inducible, and include, but are not limited to, the $\beta$-lactamase promoter (Villa-Komaroff, et al., 1978, Proc. Natl. Acad. Sci. 75:3727–31), the tac promoter (DeBoer, et al., 1983, Proc. Natl. Acad. Sci. 80:21–25), lac UV5, $\lambda P_L$, T7, and trp promoters.

Alternatives to isolating a CP gene include, but are not limited to, chemically synthesizing the gene sequence itself from a known sequence or making cDNA to the RNA which encodes the CP gene. Other methods are possible and within the scope of the invention.

In addition to promoter sequences, the CP expression vectors preferably contain specific initiation signals for efficient translation of inserted coat protein sequences. One such signal, referred to as the Shine-Dalgarno sequence, acts as a ribosome binding site that is necessary for efficient translation of RNA. In *E. coli*, the ribosome binding site includes an initiation codon (ATG) and a sequence of 3–9 nucleotides in length located 3–11 nucleotides upstream from the initiation codon (e.g., of the CP gene); on average, six out of eight nucleotides in the mRNA match this sequence: 5'-UAAGGAGG-3'. Transcription termination signals (downstream of the CP gene), selectable markers such as genes encoding antibiotic resistance, and a gene providing for expression of lysozyme (which, inter alia, aids in later purification of the pseudovirus particle by making the bacterial cell walls less resistant to rupture) are preferably also included in the plasmid expression vectors. In the BH21 (DE3) system T7 lysozyme is apparently also a stringent control for "leaky" T7 polymerase expressed from the lysogenic gene for the T7 RNA polymerase, since it functions to bind T7 polymerase.

In a specific embodiment, a recombinant expression vector provided by the invention, encoding a plant virus CP or functional derivative thereof, comprises the following, operatively linked components: a promoter which controls the expression of the CP or functional derivative thereof, a translation initiation signal, a DNA sequence encoding the CP or functional derivative thereof, and a transcription termination signal. In a preferred aspect, the above components are present in 5' to 3' order as listed above.

In another specific embodiment, described in the examples sections herein, the gene encoding the TMV CP is inserted downstream of both the T7 promoter from phage T7 gene 10 and the translational initiation signal (Shine-Dalgarno site) from gene 10 of this phage. As described infra, both wild type CP gene sequences (plasmid pET301) and CP sequences optimizing for *E. coli* codon usage (plasmid pET302) were used, as were CPs with changes in the penultimate amino-terminal Ser (the N-formyl methionine is removed by post-translational processing) to either Ala, Pro, or Asp. A T7 RNA polymerase terminator and a colE1 replicon were also included in the expression vector. In this embodiment, T7 RNA polymerase transcribes the CP sequence. The T7 RNA polymerase is produced from a chromosomally integrated sequence (a λ derivative lysogen) under the control of an inducible promoter, lac UV5. Thus, when lac UV5 transcription is induced by IPTG, T7 RNA polymerase is produced, which in turn transcribes the CP gene to produce CP. Use of an expression vector containing the T7 promoter is preferred since it has a number of advantages contributing to efficient transcription of genes cloned adjacent to the T7 promoter. These include the strict specificity of T7 polymerase for its cognate promoter sequences, the rapid rate at which elongation proceeds and the infrequency at which premature termination of transcription occurs.

PRODUCTION OF OAS-LINKED *RNA IN THE BACTERIAL HOST

A second component of the invention is a source providing for transcription of the OAS-linked *DNA, in the same bacterial host in which the CP is expressed, whereby the expressed CP assembles into a viral particle and packages therein the OAS-linked *RNA resulting from transcription.

The viral origin-of-assembly Sequences (OAS) are an essential feature of the OAS-linked *DNA vectors as they are responsible for directing the encapsidation of the heterologous RNA molecules (the OAS-linked *RNA) into pseudovirus particles. OAS, as used herein, refers to an RNA sequence (or DNA encoding such an RNA sequence) that can be specifically recognized by plant viral CPs, and which is sufficient to direct the encapsidation by such CPs of an RNA containing the OAS. As will be apparent, the OAS need not be directly linked at the 5′ or 3′ end of the *DNA; for example, there may be some intervening sequence; what is required is that the OAS be positioned with regard to the *DNA so that, upon transcription, a ribonucleic acid is produced (OAS-linked *RNA) wherein the OAS is operatively linked to the RNA sequences of interest so as to enable the encapsidation of the RNA molecule into virus-like particles by the CP. For example, transcription termination signals should only occur downstream of the OAS-linked *DNA (transcription proceeding in an upstream to downstream direction).

The OAS-linked *DNA is preferably inserted in an appropriate vector, preferably a plasmid vector, which can direct the transcription within the bacterium of OAS-linked *DNA to form the OAS-linked *RNA. The choice of vector, and its other components (e.g., promoter, selectable marker, etc.) can be as described supra in Section 5.1, but the vector must have regulatory elements functional in and compatible with the bacterial host, and compatible with the CP expression vector also present in the host. Such an OAS-linked *DNA vector preferably comprises the following operatively linked components: promoter, OAS, *DNA, and transcriptional termination signal. In one embodiment, the foregoing components are present in 5′ to 3′ order in which they are listed. In an alternative embodiment, the OAS-linked ,DNA vector comprises, in 5′ to 3′ order: promoter, *DNA, OAS, and transcriptional termination signal. This latter embodiment takes advantage of the fact that an OAS (e.g., the TMV OAS) can function in a bidirectional manner and can direct encapsidation when located at either the 5′ or 3′ end of the RNA; however, positioning the OAS at the 5′ end of the *DNA is preferred in order to inhibit degradation of its transcribed RNA within the cell. Thus, in designing the OAS-linked *DNA expression vectors it may be most effective to place the OAS sequences at the 5′ end of the *DNA so that newly transcribed RNA can be rapidly and efficiently assembled into viral particles. In this way, co-transcriptional encapsidation should protect the RNA with coat protein as the RNA is being synthesized, thereby circumventing problems associated with rapid RNA degradation in vivo. However, in an embodiment where the *RNA is an mRNA to be translated into protein, a 5′-OAS sequence may interfere with translation of the mRNA, unless an IRES or Shine-Dalgarno 40S/30S ribosome binding site is engineered between the OAS and *DNA. Alternatively, a self-cleavage ribozyme site may be inserted between the OAS and DNA.

In a specific embodiment, the OAS-linked *DNA vector further comprises a polylinker region, comprising a variety of restriction endonuclease cleavage sites, situated just 5′ or 3′ to the *DNA. In a preferred aspect, the OAS-linked ,DNA expression vector also contains a selectable marker gene, such as one encoding antibiotic (tetracycline, chloramphenicol, neomycin, etc) resistance.

In a preferred aspect, the RNA component of the OAS-linked *RNA is a mRNA encoding a protein of interest, and thus, preferably, to facilitate eventual translation thereof (see Section 5.4) a Shine-Dalgarno sequence is incorporated before the coding sequence in the *DNA.

The vectors may optionally and preferably also provide for expression of lysozyme. In a specific aspect, when using the T7 promoter system it may also be useful to express the T7 lysozyme protein, since it functions to bind T7 polymerase and inhibit low level constitutive expression by T7 polymerase. It is also preferred to express T7 lysozyme since this results in bacterial cells that are more fragile due to degradation of the *E. coli* peptidoglycan wall by lysozyme. This feature becomes useful at later stages when the bacterial cells are lysed as a step in the purification of viral particles. The T7 lysozyme gene may be expressed in the bacterial host cell either chromosomally or episomally.

As discussed supra for the CP expression vectors, methods which are well known to those skilled in the art can be used to construct bacterial vectors containing OAS-linked *DNA and appropriate transcriptional control sequences. These methods include in vitro recombinant DNA techniques (see, for example, Sambrook et al., 1989, Molecular Cloning, A Laboratory Manual, 2nd. Ed., Cold Spring Harbor Laboratory, N.Y.).

In a specific embodiment, the promoter directing the transcription of the OAS-linked *DNA is inducible and is the same promoter as that which, present on a different plasmid, directs CP gene expression. Alternatively, the CP gene promoter may be a different inducible promoter, or may be a constitutive promoter, or the OAS-linked *DNA promoter may be constitutive. As will be apparent, any combination of promoter types may be used.

One of the advantages of the production and packaging system provided by the present invention is that expression and packaging appear to be both sequence- and length-independent with respect to the RNA component of the OAS-linked *RNA. As a result, any DNA sequence of interest may be linked to an OAS and then transcribed and its RNA assembled into virus-like particles according to the invention. Thus, in a specific embodiment of the invention, a plasmid vector is provided comprising the following operatively linked elements: bacterial promoter, polylinker, OAS, transcriptional termination signal. In one embodiment, the foregoing elements appear in 5' to 3' order in which they are listed above. In another embodiment, the vector comprises the following, listed in 5' to 3' order: bacterial promoter, OAS, polylinker, transcriptional termination signal. Such vectors facilitate the insertion of any DNA sequences of interest, by virtue of the polylinker region containing a variety of restriction endonuclease cleavage sites into which the foreign *DNA may be inserted.

The selection of specific plant viral OAS sequences for use will depend on what plant viral CPs are being expressed in the bacterial host cell. It is important to keep in mind that the viral OAS sequences and viral CPs must be functionally compatible with one another for efficient assembly of OAS-linked *RNA into virus particles, i.e., the CP expressed must be able to undergo particle assembly and to recognize the OAS for encapsidation therein. OAS sequences which can be used thus include but are not limited to those of rod-shaped plant viruses including the tobraviruses, tobamoviruses, and potexviruses, with a TMV OAS most preferred. In a preferred aspect, the OAS and CP sequences are derived from the same strain of virus.

Perhaps the most well-defined of the origin-of-assembly sequences is that comprising the TMV OAS (see, e.g., Turner et al., 1988, J. Mol. Biol. 203(3):531–47; Turner and Butler, 1986, Nucl. Acids Res. 14(23):9229–42). Experiments with TMV have defined an approximately 440 nucleotide sequence, located 1 Kb from the 3' end of viral genomic RNA, that comprises the OAS sequence (FIG. 10; SEQ ID NO:5). This region is found to contain three regions predicted to form three stable hairpin stem-loops (Zimmern, D., 1983, EMBO J. 2:1901–07), and it has been shown that coat protein 20S "disks" initially bind to loop 1 (the 3' most) during viral assembly. It has also been demonstrated using in vitro packaging assays and mutant assembly origin transcripts (Turner, D. R., et al., 1988, J. Mol. Biol. 203:531–47), that rapid and specific assembly initiation may occur in the absence of loop 2 and 3, but that loop 1 sequences, which consist of about 75 nucleotides (FIG. 11; SEQ ID NO:6) are necessary and sufficient for encapsidation of heterologous RNA sequence. It is these 75 nucleotides that are the preferred OAS sequences for use in construction of OAS-linked *DNA expression vectors.

In other embodiments of the invention, an OAS other than the TMV OAS discussed above can be used. For example, cowpea strain TMV has an OAS in the middle of its CP gene (Meshi et al., 1981, Mol. Gen. Genet. 184:20–25) which can be used; the CP gene (containing the OAS) can thus be ligated to a *DNA to form an OAS-linked *DNA. In this embodiment, the OAS-linked *DNA would also function as the CP source, obviating the need for an additional source of CP. In another specific embodiment, the OAS at the 5' end of the potexvirus papaya mosaic virus RNA (Lok and Abou-Haidar, 1986, Virology 153:289–96) can be used.

In a preferred aspect of the invention, the OAS-linked *RNA and CP are produced from different expression vectors within the bacterial host. However, in an alternative embodiment, the CP gene can be incorporated in and expressed from the vector also producing the OAS-linked *RNA.

In specific embodiments of the invention detailed in the examples sections, a two-part approach is used to generate OAS-linked *RNA: Firstly, T7 RNA polymerase is expressed under the control of an inducible promoter such as lac UV5; secondly, a plasmid vector expresses the OAS-linked *DNA under the control of a T7 RNA promoter. Thus, when T7 RNA polymerase is expressed upon induction by, e.g., IPTG, the expressed T7 RNA polymerase will recognize the T7 promoter and transcribe the OAS-linked *DNA. In the specific embodiment detailed in the examples section, the OAS-linked *DNA vector contained the T7 promoter followed by the $\beta$-glucuronidase (GUS) gene cassette. The TMV OAS sequence and a T7 terminator were located at the 3' side of the GUS coding sequence. As detailed infra, a third expression vector supplied the CP for encapsidation, also expressed under control of the T7 promoter.

In another specific embodiment of the invention detailed in the examples infra, OAS-linked *RNA was produced from a plasmid containing the chloramphenicol acetyl transferase (CAT or $Cm^r$) gene followed by the TMV OAS. Low level constitutive transcription was from the *E. coli* promoter of the $Cm^r$ gene.

BACTERIAL HOSTS

Although *E. coli* is the preferred host organism, other strains of bacteria including but not limited to Salmonella spp., *B. subtilis*, and transformable Cyanobacteria (Synecococcus, Anabena, *Anacystis nidulans*) may be used for expression of OAS-linked *RNA and CP. The choice of bacterial strains will depend on which expression vectors (whether episomal or chromosomally integrated) are used for expression of viral CP and to direct the transcription of OAS-linked *DNA, since the regulatory elements of the vectors must be functional in and compatible with the bacterial host and any other vectors present. For instance, promoters, transcriptional termination signals, and origins of replication (for plasmids) should be chosen that are functional in the bacterial strain chosen, based on knowledge common in the art or readily available to the skilled artisan. As another example, if the expression of OAS-linked *DNA is under the control of the $\lambda P_L$ promoter, the cIts857 repressor protein should be supplied by the host organism (or by expression of a recombinant plasmid therein). Similarly, if expression is controlled by a T7 promoter, a source of T7 RNA polymerase should be available in the host cell. As stated supra, the host bacterium may contain the CP DNA sequence and OAS-linked *DNA constructs both episomally or both chromosomally integrated or one episomally and one chromosomally. The recombinant molecules can be introduced into the host bacterial cells via transformation, transfection, infection, electroporation, or any other method known in the art.

In a specific embodiment of the invention detailed in the examples herein, plasmids encoding and capable of expressing TMV CP and capable of transcribing OAS-linked ,DNA sequences are transformed into a host bacterial strain, referred to as *E. coli* BL21 (DE3) pLysE that contains a $\lambda$ lysogen in which the structural gene for bacteriophage T7 RNA polymerase is expressed when the inducer IPTG (isopropyl-$\beta$-D-thiogalactopyranoside) is added to the medium (Studier et al., 1990, Meth. Enzymol. 185:62–89). This particular strain of bacteria also contains the plasmid vector pACYC184 which is a p15A replicon and (as pLysE) carries the T7 lysozyme structural gene. The T7 lysozyme binds to the T7 RNA polymerase and inhibits the basal level of its activity that results from transcription from the lac UV5 promoter even in the absence of the IPTG inducer. As stated supra, the lysozyme also makes the cells more fragile since it degrades the peptidoglycan wall of the bacterial cells. In this particular system, induction of T7 RNA polymerase by addition of IPTG activates expression of OAS-linked ,DNA under the control of the T7 promoter. A second expression plasmid, which expresses CP under the control of the T7 promoter also commences expression; thus, assembly of OAS-linked RNA molecules into viral particles ensues.

PRODUCTION AND PURIFICATION OF VIRAL PARTICLES AND OAS-LINKED *RNA

Bacterial cells can be grown in a variety of different culture media known in the art, depending on the particular host cell being used. In a specific, preferred embodiment wherein plasmid vectors containing antibiotic resistance genes are employed, the appropriate antibiotics are added depending on the antibiotic resistant genes carried by each of the viral CP and OAS-linked *DNA vectors. In an embodiment in which the vectors of the invention comprise inducible promoters, inducers of the promoter activity, e.g., IPTG for the lac UV5 promoter, are added to the growth media when desired to activate transcription from the vectors.

Purification of assembled viral particles from bacterial cells can be carried out using a number of different methods. To keep virus-like particles intact during purification, all procedures should avoid shear force and detergents. Standard cleared lysate protocols with Triton X-100 should be avoided. Solutions should preferably also contain protease inhibitors such as phenylmethyl sulfonyl fluoride (PMSF), pepstatin, N-tosyl-1-phenylalanine chloromethyl ketone (TPCK), and ethylene diamine tetraacetic acid (EDTA) or other divalent cation chelators that would function to inhibit proteases. In particular embodiments, one of the following procedures may be used: (a) osmotic shock in the presence of sucrose (preferred); (b) sucrose pad centrifugation of cleared cell lysate; or (c) immunoaffinity with anti-CP antibody. In another embodiment, a freeze-thaw procedure may be useful to lyse the bacterial cells.

By way of example but not limitation, to purify assembled pseudovirus particles, the bacterial cells can be pelleted by centrifugation and then resuspended in a buffered solution such as TE buffer (10 mM Tris-HCl (pH 7.5), 1 mm EDTA)) containing lysozyme. After cell lysis, a second centrifugation step is carried out to remove cell debris. Pseudovirus particles may be further purified from cleared cell lysate using a number of different methods. For instance, an immunoaffinity column using anti-CP antibodies may be used to further enrich for virus particles. Alternatively, the cell lysate may be centrifuged through a sucrose cushion or gradient and the purified virus particles may be resuspended in TE buffer (10 mM TrisHCl (pH 7.5), 1 mM EDTA). In a preferred aspect, the osmotic shock procedure described in Section 6.1.2 is used.

To purify the chimeric OAS-linked *RNA from pseudovirus particles, any procedure known to a skilled artisan may be employed. Preferably, an SDS/phenol extraction is done to remove proteins, followed by an ethanol precipitation of the RNA.

To confirm that the RNA sequences of interest have been properly expressed and encapsidated within viral CPs according to the present invention, various assays known in the art may be performed, including but not limited to Northern (dot) blots or PCR (polymerase chain reaction) using reverse transcriptase, using as probe/primers radioactively labeled DNA fragments representative of OAS-linked DNA sequences, or the foreign *DNA.

In some cases, it may be desirable to cleave the OAS-linked sequences from the chimeric RNA prior to use. For example, an OAS sequence located at the 5′ end of the RNA could block legitimate translation initiation on *RNA or initiate translation from an AUG sequence within the OAS, resulting in a fusion protein which may also not include the desired protein sequences due to initiation not occurring in the proper reading frame. Even if OAS translational initiation sequences can be removed without affecting packaging function, the presence of the OAS may impede the efficiency of translation of the RNA into the protein of interest. Targeted cleavage, resulting in removal of the OAS sequences, may be accomplished, e.g., by use of RNAse H as follows: the OAS-linked *RNA is incubated with a DNA oligomer that binds by virtue of sequence complementarity to the region of the RNA molecule located between the OAS sequence and the RNA sequence of interest. The short region of duplex DNA/RNA that results serves as a substrate for cleavage by the DNA/RNA specific nuclease RNase H. Alternatively, recombinant RNA molecules may be designed to self-cleave by incorporation of a ribozyme domain and recognition sequence for cleavage between the OAS sequence and the DNA sequence of interest. In a different specific embodiment, a sequence-specific cleavage site may be incorporated into the OAS-linked *RNA in between the OAS and the *RNA, or a eukaryotic ribosome landing site (IRES) may be inserted between the OAS and *DNA.

USES OF ENCAPSIDATED RNA

The single stranded RNA packaging system is a convenient and efficient method for production and storage of large amounts of a particular RNA of interest. The system is RNA-sequence and -length independent, and encapsidation of RNA molecules into virus-like particles protects the RNA molecules from substantial degradation by RNases. The pseudovirus particles are easily purified from bacterial cell lysates and, once purified, may be stored for indefinite periods of time in buffer at room temperature. At the desired time, the RNA can be extracted from pseudovirus particles for use.

The uses of the single stranded RNA packaging system are broad and involve almost any of the techniques used in molecular biology that involve manipulation of RNA. For example, in an embodiment where the *RNA of the OAS-linked *RNA is a mRNA encoding a protein of interest, the recombinant RNA molecules packaged according to the present invention may be released from particles and used in in vitro translation reactions to produce the encoded protein of interest. Alternatively, the packaged recombinant RNA can comprise a sense or antisense RNA molecule that may subsequently be introduced into cells for any of a number of uses, such as to study the possible functions of the encoded protein, for therapeutic effect, etc. The packaging system of the present invention may also be used, by addition of radiolabelled nucleotides to growth media, to synthesize radioactively labeled RNA fragments corresponding to the OAS-linked *DNA that may be used as hybridization probes, e.g., for northern or Southern blot analysis.

In an alternative embodiment, the pseudovirus particles produced according to the present invention can be introduced directly into animal, plant, fungal, or prokaryotic cells as a means of directly delivering the RNA encapsidated therein, to achieve uncoating and concomitant translation within the cells. Introduction into the cell can be accomplished by any methods known in the art, e.g., by electroporation, or PLO/PEG (poly-L-ornithine/polyethylene glycol) inoculation into spheroplasts or protoplasts in plants. In another embodiment, CP derivatives which contain a surface ligand can effect delivery into animal cells via receptor-mediated endocytosis.

KITS

Kits containing one or more components for carrying out the present invention are also provided. Such a kit comprises in one or more containers component(s) for carrying out the invention. For example, such a kit can comprise container(s) having plasmid or other vectors for production of CP and production of OAS-linked *RNA, as described in Sections 5.1 and 5.2, bacteria containing one or more of the foregoing vectors or chromosomally containing a CP gene or OAS-linked *DNA. In a specific embodiment, a kit comprises in a first container a bacterium with either a chromosomally integrated or episomal CP gene under the control of preferably an inducible promoter; and in a second container a plasmid vector functional in the bacterial host that is capable of directing the transcription of OAS-linked *DNA into OAS-linked *RNA. In a preferred aspect, the second container contains a plasmid vector comprising the following operatively linked components: a promoter, polylinker, OAS, transcriptional termination signal. In one embodiment, the foregoing components are present in 5′ to 3′ order in which they are listed above. In another embodiment, the plasmid vector comprises in 5′ to 3′ order: a promoter, OAS, polylinker, transcriptional termination signal.

EXAMPLES

MATERIALS AND METHODS

PLASMIDS AND BACTERIAL STRAINS

The host bacterial strain was *E. coli* BL21 (DE3). *E. coli* BL21 is F+, ompT, $r_{\beta}^{-}$, $m\beta-$. DE3 is a λ derivative which carries a DNA fragment containing the lacI gene, the lac UV5 promoter, the beginning of the lacZ gene, and the gene for T7 RNA polymerase. The bacterial strain was originally provided by the Brookhaven National Research Laboratory and is a λ lysogen in which the structural gene for bacteriophage T7 RNA polymerase is expressed from the lac UV5 promoter when the inducer IPTG is added to the medium (Studier et al., 1990, Meth. Enzymol. 185:62–89). The lysogenic host strain also contains the plasmid vector pACYC184 (Pouwels et al., 1985, in Cloning Vectors, Elsevier Science Publishers, Amsterdam, p. I-A-iv-9) which is a p15A replicon and, as pLysE (Studier et al., 1990, Meth. Enzymol. 185:60–89), carries the T7 lysozyme structural gene expressed from the tet promoter. The lysozyme functions to bind to the T7 RNA polymerase and inhibit the low level of constitutive transcription which occurs from the lac UV5 promoter even in the absence of the IPTG inducer. The lysozyme also makes the cells more fragile since it degrades the peptidoglycan wall of the *E. coli* cells.

As part of the expression system, a source of TMV CP must be supplied. Various TMV CP structural genes (including derivatives thereof) were cloned into plasmid vector pET3a (FIG. 6). pET3a contains a T7 promoter from phage T7 gene 10 as well as the translational initiation signal (including the prokaryotic Shine-Dalgarno site) from gene 10 of this phage. The pET3 plasmid series also contains a T7 RNA polymerase terminator and is a ColE1 replicon, which is compatible with the pACYC184/p15A replicon described above. Between the T7 promoter and terminator are NdeI and NheI sites for the insertion and cloning of sequences to be transcribed by the T7 RNA polymerase.

An expression plasmid for production of native TMV coat protein using the native codons of the eukaryotic virus was made by digesting a full-length clone of TMV in the plasmid pTMV210 (a gift from W. O. Dawson, Lake Alfred University of Florida) with NsiI, followed by treatment with T4 DNA polymerase to "chew back" 3′ protruding termini, and subsequent digestion with DraI. The resulting fragment was inserted into SmaI-digested pGEM3Z (Promega, Madison, Wis.), and the resulting KpnI-BamHI CP-containing fragment was inserted (after trimming of the KpnI site to make blunt ends) into pET3a. The resulting plasmid, pET301, produces the native TMV CP (encoding the N-terminal Met-Ser of the U1 strain of TMV) from a T7 promoter when IPTG is added to induce high level expression of the T7 RNA polymerase gene (from DE3). Another plasmid (kindly provided by Joel Haynes) produces the native TMV CP of the U1 strain (Haynes et al., 1986, Biotechnology 4:637–641). This latter plasmid contains an entirely synthetic TMV CP gene insofar as the codons have been optimized for *E. coli* expression. Once again, an EcoRI-BamHI cassette of this gene was trimmed down and cloned into pET3a to produce pET302.

Plasmids were also constructed that coded for coat proteins in which the serine at the second amino acid position was replaced by alanine, aspartic acid or proline. The resulting plasmids were designated pETAla301, pETAsp301 and pETPro301, respectively. The site directed mutagenesis of the 5′ end of the gene encoding TMV coat protein was done by PCR reactions using the following primers:

1. for changing Ser(2) to Ala; 5′ primer 5′-GCCATGGCTTACAGTATCACTACT-3′(SEQ ID NO:1); 3′primer 5′-GGTCGACCTCAAGTTGCAGGACCA-3′(SEQ ID NO:2).
2. for changing Ser(2) to Asp; 5′ primer 5′-GCCATGGACTACAGTATCACTACT-3′ (SEQ ID NO:3); 3′ primer was that of SEQ ID NO:2.
3. for changing Ser(2) to Pro; 5′ primer 5′-GGCATGCCGTACAGTATCACTACT-3′ (SEQ ID NO:4); 3′ primer was that of SEQ ID NO:2.

Two strategies were used to create substrate transcripts containing the TMV origin-of-assembly (OAS)

sequence for encapsidation by TMV coat protein in situ. The first system used the chloramphenicol acetyl transferase (CAT; $Cm^r$) gene in the plasmid pLysE, which also harbors the T7 lysozyme gene. The unique EcoR1 site in the $Cm^r$ gene was cleaved and an EcoR1 fragment from plasmid pJII102 (Gallie et al., 1987, Science 236:1122–24) containing the 3′ half of the chloramphenicol acetyl transferase ($Cm^r$) gene and the TMV assembly origin (OAS) (an ~440 nucleotide sequence, from bases 5118–5550 of the viral RNA sequence; Zimmern, 1983, EMBO J. 2:1901–07; FIG. 10, SEQ ID NO:5) was inserted into the opened EcoR1 site of pLysE to generate pLys102 (FIG. 7). Thus, low level constitutive transcription from the *E. coli* promoter of the $Cm^r$ gene, used as a selectable marker for the plasmid pLysE, created a functional chloramphenicol acetyl transferase mRNA followed by the TMV OAS, in turn followed by the repeated remnant 3′ terminal fragment of the original chloramphenicol acetyl transferase selectable marker gene. Transcripts were thus expected to be 1.7 kb in length with an internal OAS.

Figure 8:
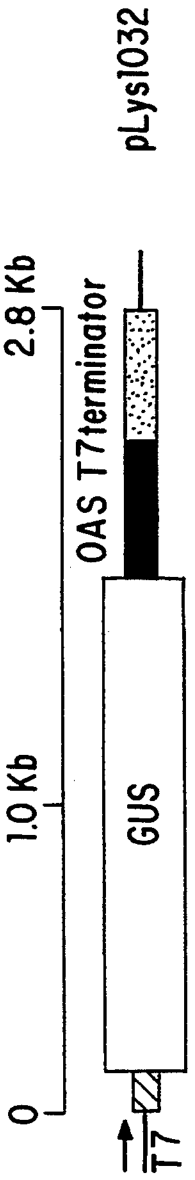
FIG. 8. Vector providing OAS-linked ,DNA. A schematic diagram of a portion of the pLys1032 vector providing the transcript to be packaged in *E. coli*, comprising the OAS-linked GUS DNA, is shown. OAS shows the origin of assembly sequence of TMV. The hatched area shows the synthetic poly (CAA) leader.

A second approach to create OAS+RNA for encapsidation with TMV coat protein in situ used a T7 promoter-poly (CAA) leader-GUS gene cassette derived from the plasmid pJII1032 (a pUC19 derivative which contain *E. coli* β-glucuronidase (GUS); see Wilson, T. M. A., et al., 1990, in Post-Transcriptional Control of Gene Expression, McCarthy and Tuite (eds.), NATO-ASI Series, Vol. H49, pp. 261–75), to which was attached a SalI-HindIII cassette containing the TMV OAS (an ~440 nucleotide sequence, from bases 5118–5550 of the viral RNA sequence; Zimmern, 1983, EMBO J. 2:1901–07; FIG. 10; SEQ ID NO:5) and a T7 terminator at the 3′ side of the GUS gene. The whole EcoRI-HindIII fragment was then modified and cloned into a unique HindIII site in the plasmid pLysE to create pLys1032 (FIG. 8). Transcripts derived from the T7 promoter are expected to be approximately 2.5 kb in length and contain a 3′ terminal TMV origin-of-assembly sequence.

PURIFICATION OF PSEUDOVIRAL PARTICLES FROM *E. COLI*

Bacteria were grown in 100 ml of media at 37° C. for 4 hours. Cells were induced by 0.4 mM IPTG for 6 hours at room temperature. Bacteria were harvested by centrifugation at 8K rpm at 4° C. for 15 minutes. The bacterial cell pellet was resuspended in 1 ml of TE (10 mM Tris-HCl (pH 7.5), 1 mM EDTA) and then lysozyme solution was added to 1 mg/ml. This suspension was incubated at RT for 5–10 minutes followed by addition of four volumes of TE (pH 7.5). DNase I was added and the suspension was incubated until it was no longer viscous. The suspension was centrifuged at 10K rpm, at 4° C. for 20 minutes to remove cell debris and the supernatant was loaded onto a sucrose gradient (10–40%) and spun in a Beckman 45 Ti rotor at 40K rpm, at 4° C for 4 hours. The pellet from the bottom of the sucrose gradient was dissolved in 1 ml of TE (pH 7.5) and this sample was used for electron microscopy.

EXTRACTION OF RNA AND NORTHERN DOT BLOTS

Figure 9:
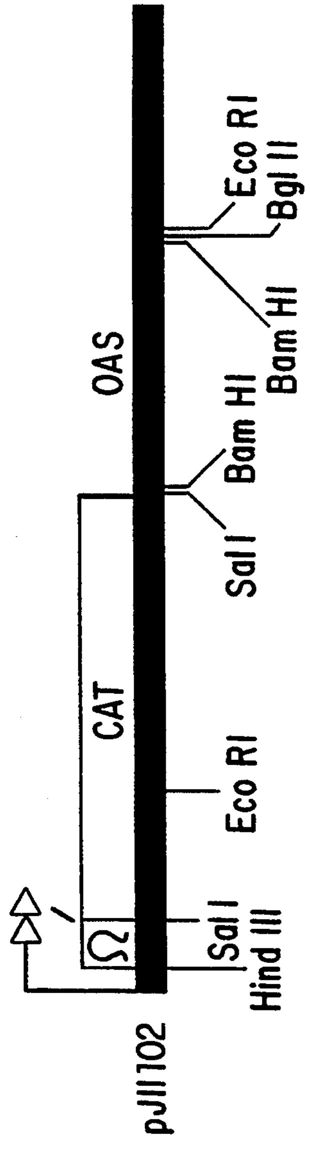
FIG. 9. Schematic diagram of OAS probe. A schematic diagram is shown of a portion of pJII102 (Gallie et al., 1987, Science 236:1122–24) comprising the sequence from which the OAS hybridization probe was derived. Ω′ represents TMV leader derivative (Gallie et al., 1987, Nucl. Acids Res. 15:3127).

A $^{32}P$-labelled DNA fragment containing the OAS sequence was used as a probe in northern dot blot hybridizations. The probe was derived from pJII102 (Gallie et al., 1987, Science 236:1122–24), a portion of which is shown in FIG. 9. pJII102 was digested with BamHI, run on a gel, and a small, approximately 440 bp fragment containing OAS was eluted. The fragment was nick-translated with $^{32}P$-dATP using *E. coli* DNA polymerase I and DNase I (see Sambrook et al., 1989, Molecular Cloning, A Laboratory Manual, 2nd Ed., Cold Spring Harbor Laboratory, N.Y.) The labeled probe was added to the hybridization solution.

For the dot blot hybridization, RNA was extracted from purified viral particles by phenol extraction. The RNA was precipitated by the addition of ethanol and an appropriate salt such as sodium acetate. The RNA sample was dotted onto nitrocellulose paper, which was then dried at room temperature. After denaturation and neutralization, the filter was baked at 80° C. for 2 h, prehybridized at 42° C. for 2 h, and then hybridized at 42° C. for 2 h with the nick-translated probe, washed, and exposed to film.

POLYMERASE CHAIN REACTION (PCR) AMPLIFICATION OF RNA ISOLATED FROM PSEUDOVIRUS PARTICLES

RNA samples were extracted from purified TMV-like particles as described in Section 6.1.3. The RNA samples were used as substrates for reverse transcriptase, and the resulting cDNAs were used in PCR reactions with the following pair of primers: 3′ primer of TMV OAS (5′ to 3′), 5′ CCG GTT CGA GAT CGA 3′ (SEQ ID NO:7); and 5′ primer of TMV OAS (5′ to 3′), 5′ GTT GGT CGT CAC GG 3′ (SEQ ID NO:8).

SDS PAGE ANALYSIS OF *E. COLI* PRODUCED TMV COAT PROTEIN

The TMV CP used in these particular experiments was either the *E. coli* optimized codon version of the U1 strain sequence (pET302) or native TMV U1 coat protein sequence (pET301) or the native TMV coat protein sequence PCR cloned from pTMV210 but in which the second amino acid (serine) was altered to an alanine (pETAla301). IPTG was added to the 10 ml culture when the cell density reached approximately 0.6. In the cases shown, the induction time with IPTG was 2 hours. A volume equivalent to 93 μl of original *E. coli* culture was loaded on a standard discontinuous Laemmli gel system (Laemmli, U.K., 1970, Nature 227:680) in which the resolving gel was 15% polyacrylamide and subjected to sodium dodecyl sulfate polyacrylamide gel electrophoresis (SDS PAGE). To visualize the proteins, the gel was stained with Coomassie blue. The identity of the protein bands was confirmed not only by co-migration with legitimate TMV CP (added to the marker lane 2) but also by western blotting with polyclonal antiserum raised in rabbits against native U1 TMV CP.

RESULTS EXPRESSION OF TMV VIRAL COAT PROTEINS AND PACKAGING OF RECOMBINANT RNA MOLECULES IN *E. COLI*

Figure 2:
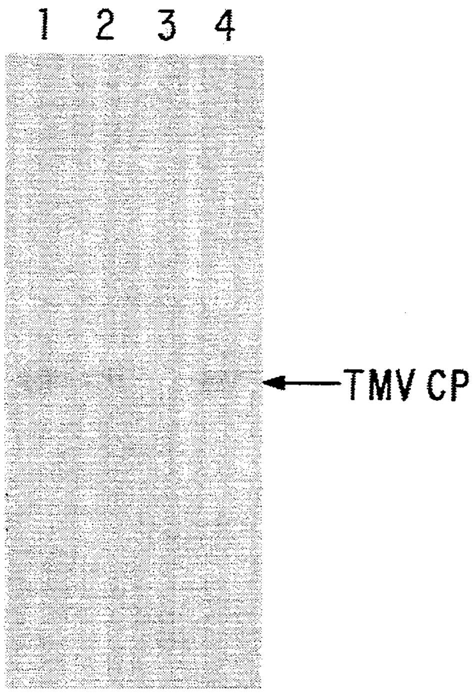
FIG. 2. Western blot analysis of TMV coat proteins expressed in *E. coli* Lanes: 1, pETAla301 (+) IPTG; 2, pET301 (+) IPTG; 3, pET301 (−) IPTG; 4, pET302 (+)IPTG.
Figure 3A:
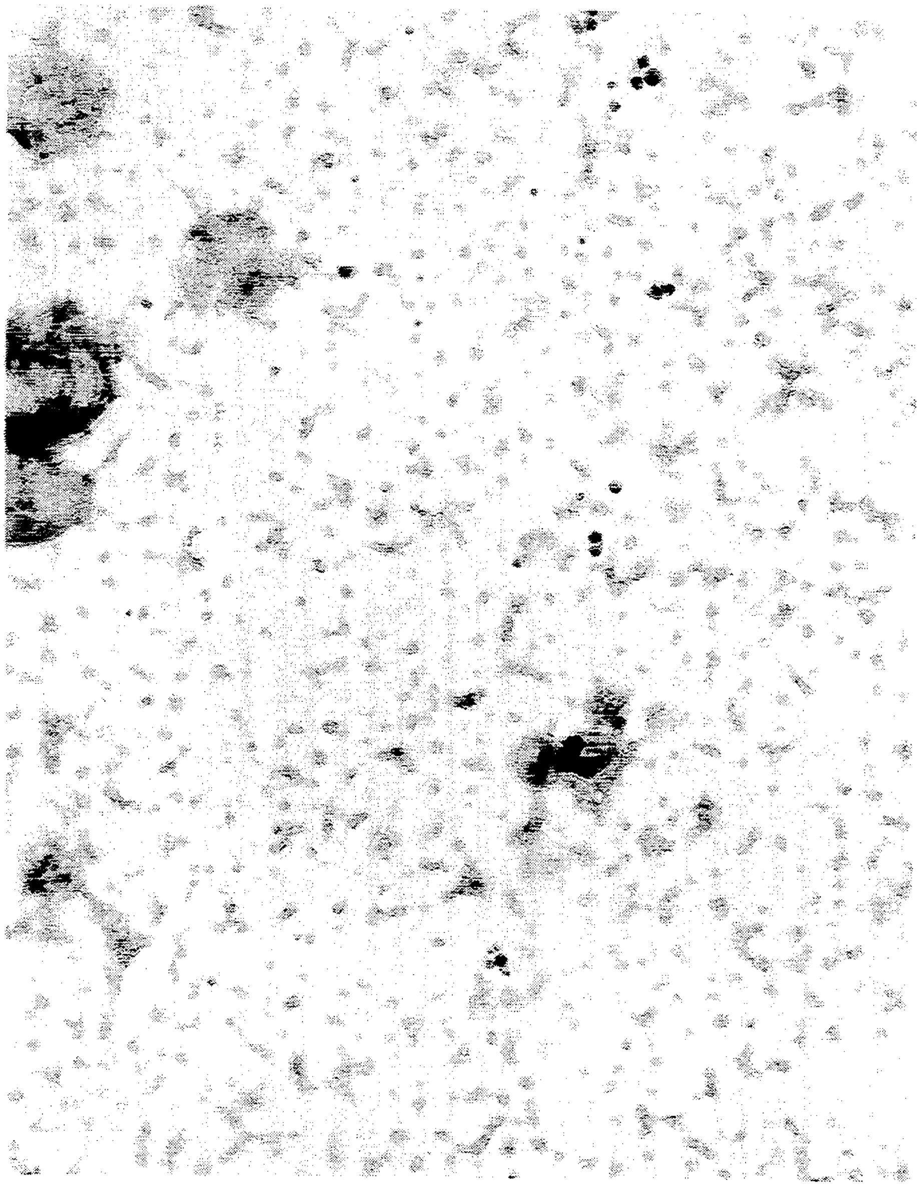
FIG. 3A-3E Electron micrographs of *E. coli*-produced TMV coat protein and TMV-like particles. Immunosorbent electron microscopy of complexes containing TMV coat protein from IPTG-induced cultures of *E. coli* transformed with pETAla301 and pLysE (negative control with CP alone; panel A), or pETAla301 and pLys102 (panels B, C, D;=CAT-OAS mRNA) was performed. Negative staining was with 1% uranyl acetate (panels A, B, C) or with 1% ammonium molybdate (panel D). Panel E shows a histogram of TMV-like particles.
Figure 3B:
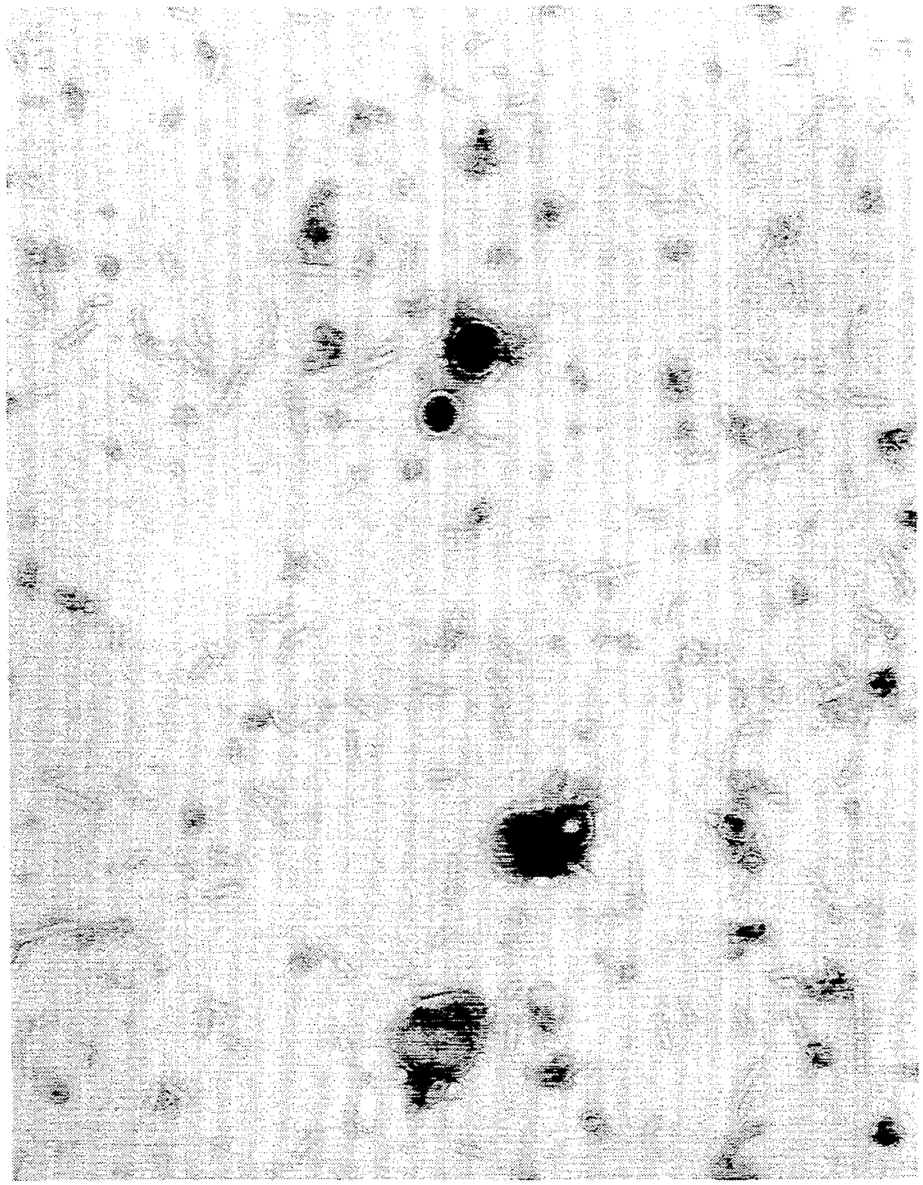
Figure 3C:
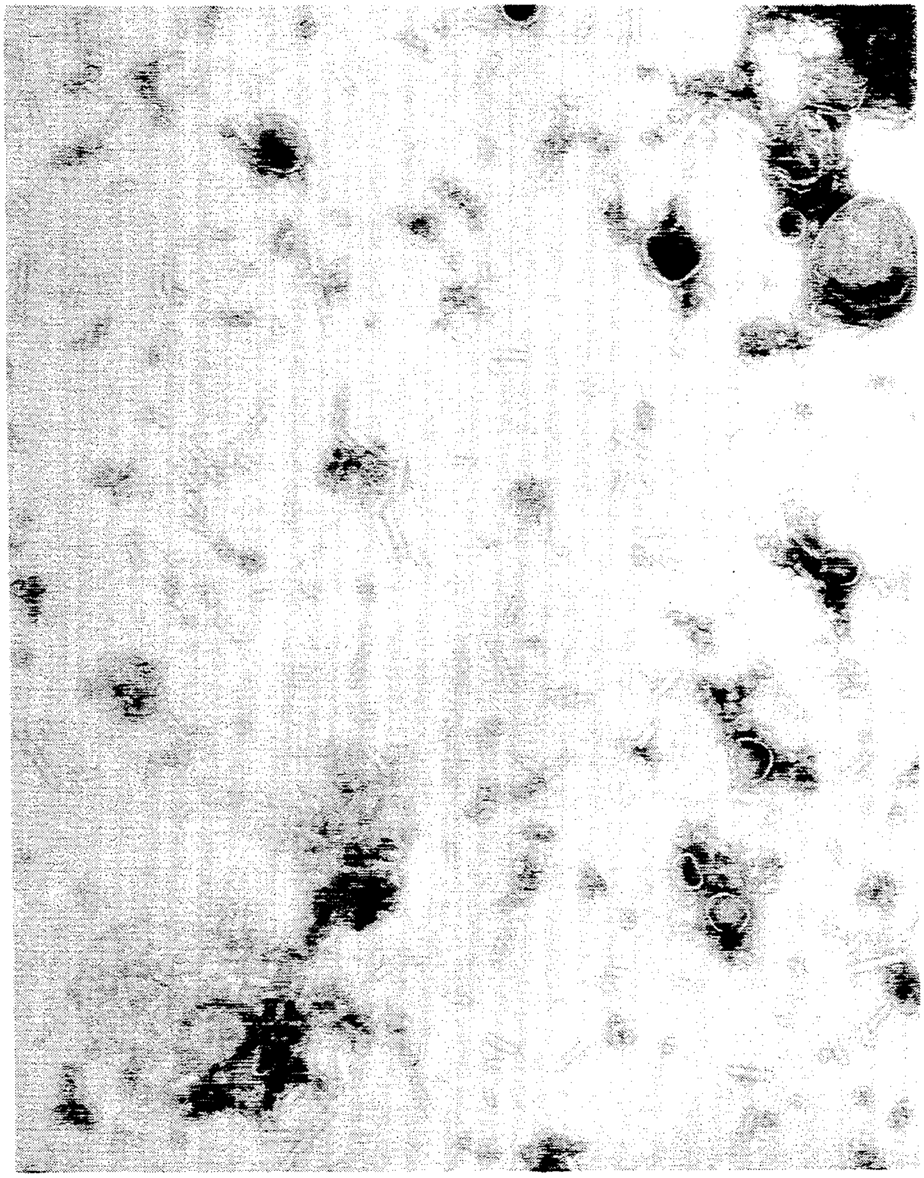
Figure 3D:
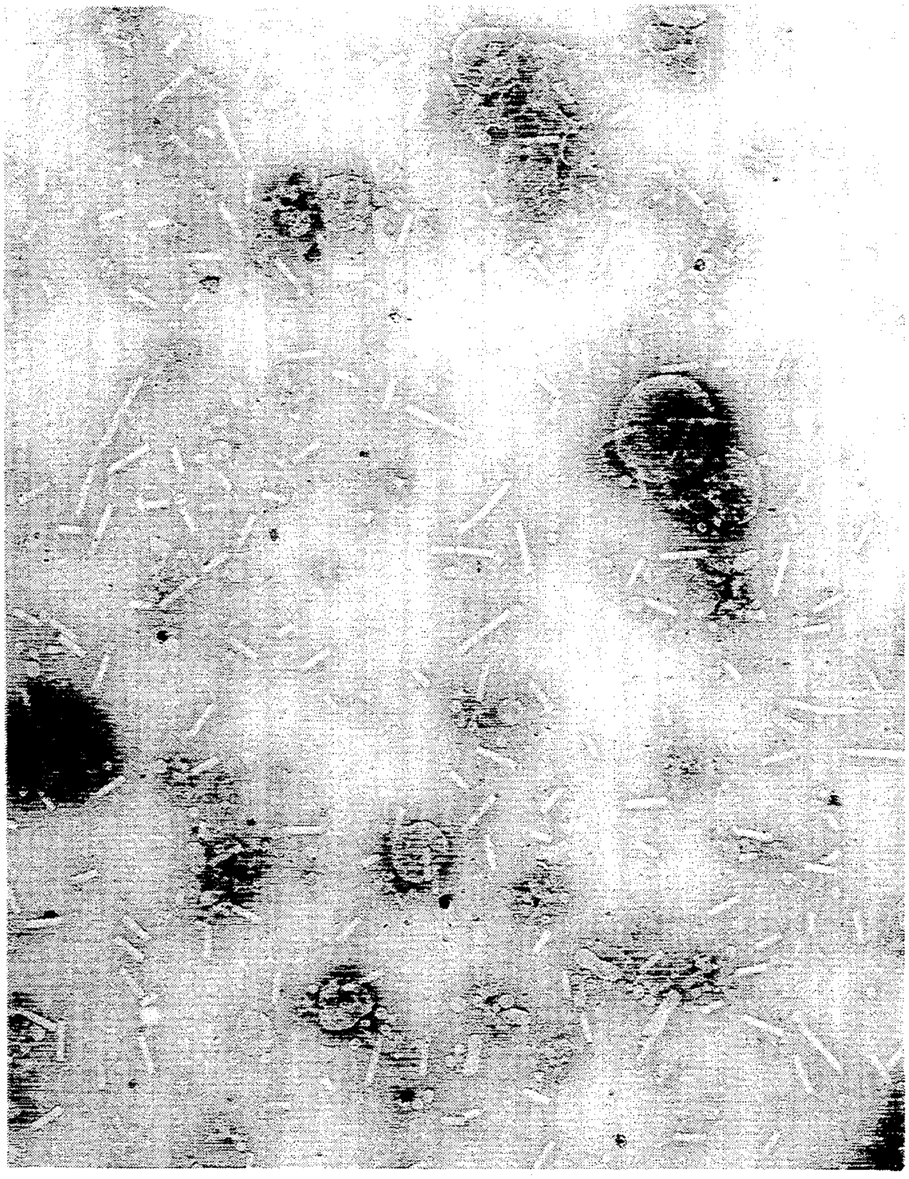
Figure 3E:
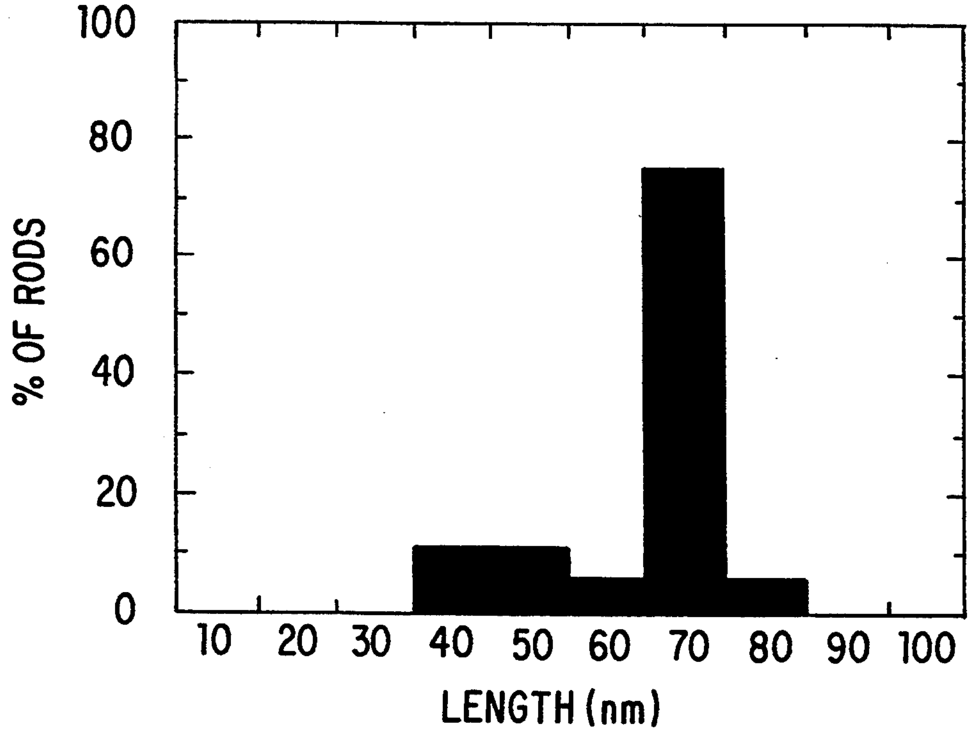

The results of SDS PAGE analysis of cleared cell lysates are shown in FIG. 1. The TMV coat protein used in these particular experiments was either the *E. coli* optimized codon version of the U1 strain sequence (pET302) or the native TMV U1 coat protein sequence (pET301) or the native TMV coat protein sequence PCR cloned from pTMV210 but in which the second amino acid (serine) is altered to an alanine. Staining with Coomassie blue clearly shows that pET301 and pETAla301 induced synthesis of 2–3 μg TMV coat protein per 93 μl of original cell culture. pET302 induced about 2 or 3 times more CP than either of the above as judged by Coomassie blue staining. The identity of these protein bands was confirmed not only by co-migration with legitimate TMV coat protein (added to the marker lane 2) but also by western blotting with polyclonal antiserum raised in rabbits against TMV coat protein (FIG. 2). The low level of signal on the Western blot in lane 2 is attributed to the fact that, even without IPTG, a low level background constitutive expression of the T7 RNA polymerase takes place despite the expression of T7 lysozyme which inhibits the activity of the enzyme.

For purposes of comparison to the in vivo assembly of particles, in vitro assembly was also attempted. All the CPs were purified extensively from induced cultures of *E. coli* in the absence of OAS+ messenger RNAs and following the procedure of Durham (1972, J. Mol. Biol. 67:289–305), were incubated with phenol extracted purified TMV RNA. Virus-purified CP was also used as a positive control. The positive control assembled and increased turbidity ($A_{310}$ nm) measurably, whereas none of the *E. coli* generated CPs functioned to assemble with TMV RNA in vitro.

Electron micrographs of *E. coli* in which each CP construct had been expressed in the absence of an OAS+RNA revealed some assembly of virus-like structures which, upon close examination, were seen to be predominantly stacked disk rods (usually viewed as products of proteolysis) which presumably contain no RNA. This observation of non-helical assembly has been confirmed by the absence of immunogold labelling with monoclonal antibodies specific for the native helical TMV structure.

With regard to in vivo particle assembly in *E. coli*, in both the presence or absence of OAS+mRNA, the proline version of the TMV coat protein, synthesized from pETPro301 clearly formed stacked disk rods as visualized in the electron microscope. We have yet to determine whether or not these rods contain RNA but their clear, striated appearance suggests a protein-only structure. Cleared cell lysates were viewed in the electron microscope and the resulting pictures are shown in FIG. 3 A–D. The native form of TMV CP as generated from plasmid pET301, when expressed without an OAS+RNA, gave a completely clean background and no apparent assembly into virus-like rods. For pETAla301, pET301, and pET302, when coat protein from any one of these plasmids was expressed in the presence of an OAS+mRNA, for either CAT or GUS, electron microscopy revealed a substantial increase in the number of short rods, as demonstrated in FIG. 3 for pETAla301. The lengths of some preparations were more homogeneous than others and complied with the predicted lengths of the rods (approximately 75 nm for CAT-OAS) resulting from transcription of the particular gene.

Figure 4:
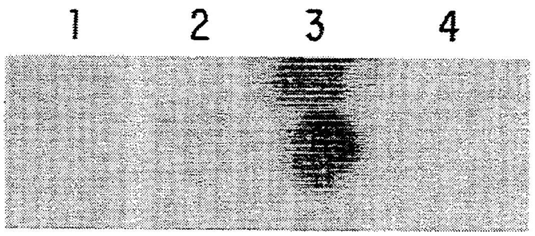
FIG. 4. Northern dot blots of RNA extracted from virus-like particles. Lanes: 1, $H_2O$ control; 2, pETAla301 and pLys102 (CAT-OAS mRNA); 3, pETAla301 and pLys1032 (GUS-OAS mRNA); 4, pLysE and pETAla301.
Figure 5:
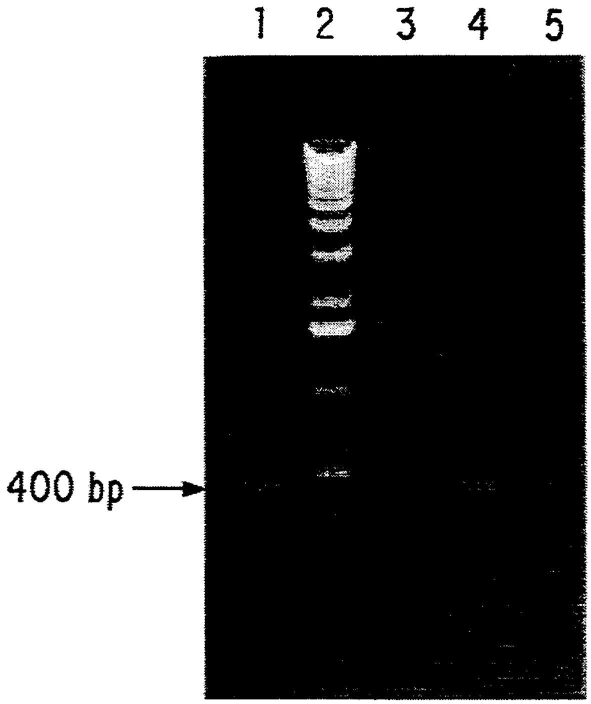
FIG. 5. PCR amplification of RNA samples isolated from pseudovirus particles by use of 5′ and 3′ primers derived from the TMV OAS sequence. Lanes: 1, TMV RNA (positive control); 2, molecular weight "markers"; 3, pLysE CAT; 4, pLys102 CAT-OAS; 5, pLys1032 GUS-OAS.

RNA was extracted from these purified particles following sucrose density gradient, cesium sulfate isopycnic gradient or sucrose pad centrifugation, and a northern dot blot was done with a TMV OAS specific probe. In the case of induction where CAT and/or GUS RNA containing the TMV origin-of-assembly sequence together with pETAla301 coat protein was expressed, the resulting rods produced RNA which gave a strong and clear signal with an OAS specific probe (FIG. 4). PCR amplification of RNA samples derived from pseudovirus particles by use of 5′ and 3′ primers from the TMV OAS sequences also allowed detection of CAT-OAS and GUS-OAS in such case (FIG. 5).

Thus, pETAla301-encoded TMV CPs assembled and packaged CAT-OAS RNA or CAA-GUS-OAS RNA into TMV-like pseudovirus particles in vivo in *Escherichia coli*.

DEPOSIT OF MICROORGANISMS

Bacteria strain *E. coli* BL21 (DE3) containing plasmid pETAla301 (an expression plasmid encoding a TMV coat protein with $Ser_2$ replaced by $Ala_2$), and plasmid pLys102 (a plasmid providing packageable CAT-OAS transcripts) was deposited on Sep. 10, 1992 with the American Type Culture Collection, 12301 Parklawn Drive, Rockville, Md. 20852, under the provisions of the Budapest Treaty on the International Recognition of the Deposit of Microorganisms for the Purposes of Patent Procedures, and assigned Accession No. 69070.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of producing and encapsidating a recombinant RNA molecule in a plant pseudovirus particle comprising culturing a bacterium containing (a) a first recombinant nucleic acid encoding a tobacco mosaic virus coat protein, and (b) a second recombinant nucleic acid that can be transcribed to produce RNA molecule comprising a tobacco mosaic virus origin-of-assembly sequence operatively linker to an RNA sequence of interest, with the proviso that the RNA sequence of interest is not a tobacco mosaic virus RNA; whereby the tobacco mosaic virus coat protein is expressed and the second recombinant nucleic acid is transcribed in the bacterium, and the coat protein assembles into a particle encapsidating the RNA molecule.

2. The method according to claim 1 in which the first recombinant nucleic acid is a plasmid vector comprising the following operatively linker components:

(a) a promoter which controls the expression of the coat protein;
(b) a translation initiation signal;
(c) a DNA sequence encoding the coat protein; and
(d) a transcription termination signal.

3. The method according to claim 1 in which the second recombinant nucleic acid is a plasmid vector comprising the following operatively linked components:

(a) a promoter;
(b) a DNA sequence that can be transcribed under the control of the promoter in the bacterium to produce the RNA molecule comprising the origin of assembly sequence operatively linked to the RNA sequence of interest; and
(c) a transcription termination signal.

4. The method according to claim 1 in which the first recombinant nucleic acid comprises the native coat protein gene of a tobacco mosaic virus.

5. The method according to claim 1 in which the first recombinant nucleic acid comprises a sequence encoding a native coat protein of a tobacco mosaic virus, which sequence has been optimized for translation in *Escherichia coli*.

6. The method according to claim 1 in which the origin of assembly sequence comprises the sequence.

7. The method according to claim 1 in which the origin of assembly sequence comprises the sequence.

8. The method according to claim 1 in which the RNA sequence of interest is a messenger RNA sequence encoding a protein of interest.

9. A method of producing and encapsidating a recombinant RNA molecule in a plant pseudovirus particle comprising culturing a bacterium containing (a) a first plasmid vector comprising the following operatively linked components: (i) a first promoter which controls the expression of a first DNA sequence encoding a tobacco mosaic virus coat protein, (ii) a translation initiation signal, (iii) the first DNA sequence encoding the coat protein, and (iv) a first transcription termination signal; and (b) a second plasmid vector comprising the following operatively linked components: (i) a second promoter, (ii) a second DNA sequence that can be transcribed under the control of the second promoter in the bacterium to produce an RNA molecule comprising a tobacco mosaic virus origin of assembly sequence operatively linker to an RNA sequence of interest, with the proviso that the RNA sequence of interest is not a tobacco mosaic virus RNA, and (iii) a second transcription termination signal; whereby the coat protein is expressed and the second DNA sequence is transcribed in the bacterium, and the coat protein assembles into a particle encapsidating the RNA molecule.

10. The method according to claim 9 in which the bacterium is an *Escherichia coli.*

11. The method according to claim 9 in which the first promoter and the second promoter are inducible promoters.

12. The method according to claim 9 in which the first promoter and the second promoter are T7 RNA promoters, and the bacterium further contains a third DNA sequence comprising a T7 RNA polymerase coding sequence and an inducible promoter controlling the expression of the T7 RNA polymerase.

13. The method according to claim 12 in which the inducible promoter is a lac UV5 promoter.

14. The method according to claim 13 in which the third DNA sequence is chromosomally integrated.

15. The method according to claim 9 in which the RNA sequence of interest is a messenger RNA sequence encoding a protein of interest.

16. The method according to claim 9 which the first plasmid vector and the second plasmid vector each further comprises a selectable marker.

17. The method according to claim 16 in which the selectable markers are antibiotic resistance genes.

18. The method according to claim 16 in which the bacterium further contains a recombinant DNA sequence which is expressed to produce lysozyme upon culturing the bacterium.

19. A recombinant containing:

(a) a first recombinant nucleic acid encoding a tobacco mosaic virus coat protein, in which the first recombinant nucleic acid comprises a promoter sequence which controls the expression of the tobacco mosaic virus coat protein in the bacterium; and (b) a second recombinant nucleic acid that can be transcribed in the bacterium to produce an RNA molecule comprising a tobacco mosaic virus origin of assembly sequence operatively linked to an RNA sequence of interest, with the proviso that the RNA sequence of interest is not a tobacco mosaic virus RNA, in which the second recombinant nucleic acid comprises a promoter sequence which controls the expression of the RNA molecule in the bacterium.

20. A recombinant bacterium containing:

(a) a first plasmid vector comprising the following operatively linked components: (i) a first promoter which controls the expression in the bacterium of a first DNA sequence encoding a tobacco mosaic virus coat protein; (ii) a translation initiation signal; (iii) the first DNA sequence encoding the coat protein; and (i) a first transcription termination signal; and (b) a second plasmid vector comprising the following operatively linked components: (i) a second promoter; (ii) a second DNA sequence that can be transcribed under the control of the second promoter in the bacterium to produce an RNA molecule comprising a tobacco mosaic virus origin of assembly sequence operatively linker to an RNA sequence of interest, with the proviso that the RNA sequence of interest is not a tobacco mosaic virus RNA; and (iii) a second transcription termination signal.

21. The bacterium of claim 20 in which the bacterium is an *Escherichia coli.*

22. The bacterium of claim 20 in which the first promoter and the second promoter are T7 RNA promoters, and the bacterium further contains a third DNA sequence comprising a T7 RNA polymerase coding sequence and an inducible promoter controlling the expression of the T7 RNA polymerase.

23. An *Escherichia coli* containing plasmids pETAla301 and pLys102 as deposited with the ATCC and assigned Accession No. 69070.

24. A method of producing and encapsidating a recombinant RNA molecule in a plant pseudovirus particle comprising culturing a bacterium containing (a) a first recombinant nucleic acid encoding a coat protein of the U1 strain of tobacco mosaic virus in which the second amino acid from the amino terminus has been changed to an alanine, and (b) a second recombinant nucleic acid that can be transcribed to produce an RNA molecule comprising a tobacco mosaic virus origin-of-assembly sequence operatively linked to an RNA sequence of interest, with the proviso that the RNA sequence of interest is not a tobacco mosaic virus RNA; whereby the coat protein is expressed and the second recombinant nucleic acid is transcribed in the bacterium, and the coat protein assembles into a particle encapsidating the RNA molecule.

25. The method according to claim 24 in which the first recombinant nucleic acid is a plasmid vector comprising the following operatively linked components:

(a) a promoter which controls the expression of the coat protein;

(b) translation initiation signal;

(c) a DNA sequence encoding the coat protein; and (d) a transcription termination signal.

26. The method according to claim 24 in which the second recombinant nucleic acid is a plasmid vector comprising the following operatively linked components:

(a) a promoter;

(b) a DNA sequence that can be transcribed under the control of the promoter in the bacterium to produce the RNA molecule comprising the origin of assembly sequence operatively linked to the RNA sequence of interest; and (c) a transcription termination signal.

27. The method according to claim 24 in which the origin of assembly sequence comprises the sequence set forth in SEQ ID NO:6.

28. The method according to claim 24 in which the origin of assembly sequence comprises the sequence set forth in SEQ ID NO:5.

29. The method according to claim 24 in which the RNA sequence of interest is a messenger RNA sequence encoding a protein of interest.

30. A method of producing and encapsidating a recombinant RNA molecule in a plant pseudovirus particle comprising culturing a bacterium containing (a) a first plasmid vector comprising the following operatively linked components: (i) a first promoter which controls the expression of a first DNA sequence encoding a coat protein of the U1 strain of tobacco mosaic virus in which the second amino acid from the amino terminus has been changed to an alanine, (ii) a translation initiation signal, (iii) the first DNA sequence encoding the coat protein, and (iv) a first transcription termination signal; and (b) a second plasmid vector comprising the following operatively linked components: (i) a second promoter, (ii) a second DNA sequence that can be transcribed under the control of the second promoter in the bacterium to produce an RNA molecule comprising a tobacco mosaic virus origin of assembly sequence operatively linked to an RNA sequence of interest, with the proviso that the RNA sequence of interest is not a tobacco mosaic virus RNA, and (iii) a second transcription termination signal; whereby the coat protein is expressed and the second DNA sequence is transcribed in the bacterium, and the coat protein assembles into a particle encapsidating the RNA molecule.

31. The method according to claim 30 in which the origin of assembly sequence comprises the sequence set for the in SEQ ID NO;6.

32. The method according to claim 30 in which the bacterium is an *Escherichia coli.*

33. The method according to claim 30 in which the first promoter and the second promoter are inducible promoters.

34. The method according to claim 30 in which the first promoter and the second promoter are T7 RNA promoters, and the bacterium further contains a third DNA sequence comprising a T7 RNA polymerase coding sequence and an inducible promoter controlling the expression of the T7 RNA polymerase.

35. The method according to claim 34 in which the inducible promoter is a lac UV5 promoter.

36. The method according to claim 35 in which the third DNA sequence is chromosomally integrated.

37. The method according to claim 30 in which the RNA sequence of interest is a messenger RNA sequence encoding a protein of interest.

38. The method according to claim 30 in which the first plasmid vector and the second plasmid vector each further comprises a selectable marker.

39. The method according to claim 38 in which the selectable markers are antibiotic resistance genes.

40. The method according to claim 38 in which the bacterium further contains a recombinant DNA sequence which is expressed to produce lysozyme upon culturing the bacterium.

41. A recombinant bacterium containing:

(a) a first recombinant nucleic acid encoding a coat protein of the U1 strain of tobacco mosaic virus in which the second amino acid from the amino terminus has been changed to an alanine, in which the first recombinant nucleic acid comprises a promoter sequence which controls the expression of the coat protein in the bacterium; and (b) a second recombinant nucleic acid that can be transcribed in the bacterium to produce an RNA molecule comprising a tobacco mosaic virus origin of assembly sequence operatively linked to an RNA sequence of interest, with the proviso that the RNA sequence of interest is not a tobacco mosaic virus RNA, in which the second recombinant nucleic acid comprises a promoter sequence which controls the expression of the RNA molecule in the bacterium.

42. The bacterium of claim 41 in which the origin of assembly sequence comprises the sequence set forth in SEQ ID NO:6.

43. A recombinant bacterium containing:

(a) a first plasmid vector comprising the following operatively linked components: (i) a first promoter which controls the expression in the bacterium of a first DNA sequence encoding a coat protein of the U1 strain of tobacco mosaic virus in which the second amino acid from the amino terminus has been changed to an alanine; (ii) a translation initiation signal; (iii) the first DNA sequence encoding the coat protein; and (iv) a first transcription termination signal; and (b) a second plasmid vector comprising the following operatively linked components: (i) a second promoter; (ii) a second DNA sequence that can be transcribed under the control of the second promoter in the bacterium to produce an RNA molecule comprising a tobacco mosaic virus origin of assembly sequence operatively linked to an RNA sequence of interest, with the proviso that the RNA sequence of interest is not a tobacco mosaic virus RNA; and (iii) a second transcription termination signal.

44. The bacterium of claim 43 in which the origin of assembly sequence comprises the sequence set for the in SEQ ID NO:6.

45. The bacterium of claim 43 in which the bacterium is an *Escherichia coli.*

46. The bacterium of claim 43 in which the first promoter and the second promoter are T7 RNA promoters, and the bacterium further contains a third DNA sequence comprising a T7 RNA polymerase coding sequence and an inducible promoter controlling the expression of the T7 RNA polymerase.

47. A kit comprising, in one or more containers:

(a) a first recombinant nucleic acid comprising a DNA sequence encoding a tobacco mosaic virus coat protein and a promoter sequence which controls the expression of the tobacco mosaic virus coat protein in a suitable bacterium; and (b) a second recombinant nucleic acid that can be transcribed in the suitable bacterium to produce an RNA molecule comprising a tobacco mosaic virus origin of assembly sequence operatively linked to an RNA sequence of interest, with the proviso that the RNA sequence of interest is not a tobacco mosaic virus RNA.

48. A kit comprising, in one or more containers:

(a) a first plasmid vector comprising the following operatively linked components: (i) a first promoter which controls the expression in a suitable bacterium of a first DNA sequence encoding a tobacco mosaic virus coat protein; (ii) a translation initiation signal; (iii) the first DNA sequence encoding the coat protein; and (iv) a first transcription termination signal; and (b) a second plasmid vector comprising the following operatively linked components: (i) a second promoter; (ii) a second DNA sequence that can be transcribed under the control of the second promoter in the suitable bacterium to produce an RNA molecule comprising a tobacco mosaic virus origin of assembly sequence operatively linked to an RNA sequence of interest, with the proviso that the RNA sequence of interest is not a tobacco mosaic virus RNA; and (iii) a second transcription termination signal.

49. A kit comprising, in one or more containers:

(a) a first plasmid vector comprising the following operatively linked components: (i) a first promoter which controls the expression in a suitable bacterium of a first DNA sequence encoding a tobacco mosaic virus coat protein; (ii) a translation initiation signal; (iii) the first DNA sequence encoding the coat protein; and (iv) a first transcription termination signal; and (b) a second plasmid vector comprising the following operatively linked components: (i) a second promoter which controls the expression in the suitable bacterium of a second promoter which controls the expression in the suitable bacterium of a second DNA sequence, (ii) the second DNA sequence, the comprises a polylinker and a sequence encoding a tobacco mosaic virus origin of assembly sequence, and (iii) a second transcription termination signal.

50. The kit according to claim 49 in which the polylinker is 5′ to the sequence encoding a tobacco mosaic virus origin of assembly sequence.

51. The kit according to claim 49 in which the polylinker is 3′ to the sequence encoding a tobacco mosaic virus origin of assembly sequence.

52. A kit comprising in one or more containers:

(a) a first plasmid vector comprising the following operatively linked components: (i) a first promoter which controls the expression in a suitable bacterium of a first DNA sequence encoding a coat protein of the U1 strain of tobacco mosaic virus in which the second amino acid from the amino terminus has been changed to an alanine; (ii) a translation initiation signal; (iii) the first DNA sequence encoding the coat protein; and (iv) a first transcription termination signal; and

53. The kit according to claim 52 in which the polylinker is 5′ to the sequence encoding a tobacco mosaic virus origin of assembly sequence.

54. The kit according to claim 52 in which the polylinker is 3′ to the sequence encoding a tobacco mosaic virus origin of assembly sequence.

55. A kit comprising in one or more containers the bacterium of claim 19.

56. The kit of claim 55 in which the bacterium is an *Escherichia coli*.

57. A kit comprising in one or more containers the bacterium of claim 20.

58. A kit of claim 57 in which the bacterium is an *Escherichia coli*.

59. A kit comprising in one or more containers the bacterium of claim 22.

60. A kit comprising, in one or more containers:

(a) a first recombinant nucleic acid comprising a DNA sequence encoding a coat protein of the U1 strain of tobacco mosaic virus in which the second amino acid from the amino terminus has been changed to an alanine, and a promoter sequence which controls the expression of the coat protein in a suitable bacterium; and (b) a. second recombinant nucleic acid that can be transcribed in the suitable bacterium to produce an RNA molecule comprising a tobacco mosaic virus of origin of assembly sequence operatively linked to an RNA sequence of interest, with the proviso that the RNA sequence of interest is not a tobacco mosaic virus RNA.

61. The kit of claim 60 in which the origin of assembly sequence comprises the sequence set forth in SEQ ID NO:6.

62. A kit comprising, in one or more containers:

(a) a first plasmid vector comprising the following operatively linked components: (i) a first promoter which controls the expression in a suitable bacterium of a first DNA sequence encoding a coat protein of the U1 strain of tobacco mosaic virus in which the second and no acid from the and no terminus has been changed to an alanine; (ii) a translation initiation signal; (iii) the first DNA sequence encoding the coat protein; and (iv) a first transcription termination signal; and (b) a second plasmid vector comprising the following operatively linked components: (i) a second promoter; (ii) a second DNA sequence that can be transcribed under the control of the second promoter in the suitable bacterium to produce an RNA molecule comprising a tobacco mosaic virus origin of assembly sequence operatively linked to an RNA sequence of interest, with the proviso that the RNA sequence of interest is not a tobacco mosaic virus RNA; and (iii) a second transcription termination signal.

63. The kit of claim 62 in which the origin of assembly sequence comprises the sequence set forth in SEQ ID NO:6.

64. A kit comprising in one or more containers the bacterium of claim 41.

65. The kit of claim 64 in which the bacterium is an *Escherichia coli*.

66. A kit comprising in one or more containers the bacterium of claim 43.

67. The kit of claim 66 in which the bacterium is an *Escherichia coli*.

68. A kit comprising in one or more containers the bacterium of claim 46.

* * * * *